(12) United States Patent
Sato

(10) Patent No.: US 10,045,763 B2
(45) Date of Patent: Aug. 14, 2018

(54) ENDOSCOPIC TREATMENT TOOL SET

(71) Applicant: OLYMPUS CORPORATION, Tokyo (JP)

(72) Inventor: Masatoshi Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/634,261

(22) Filed: Jun. 27, 2017

(65) Prior Publication Data

US 2017/0290575 A1 Oct. 12, 2017

Related U.S. Application Data

(63) Continuation of application No. PCT/JP2016/062248, filed on Apr. 18, 2016.

(30) Foreign Application Priority Data

Sep. 17, 2015 (JP) .................... 2015-184394

(51) Int. Cl.
*A61B 17/00* (2006.01)
*A61B 17/11* (2006.01)
(Continued)

(52) U.S. Cl.
CPC ...... *A61B 17/00234* (2013.01); *A61B 17/064* (2013.01); *A61B 17/068* (2013.01);
(Continued)

(58) Field of Classification Search
CPC .. A61B 2017/0649; A61B 2017/00867; A61B 2017/00862; A61B 2017/0645;
(Continued)

(56) References Cited

U.S. PATENT DOCUMENTS

2009/0125038 A1  5/2009  Ewers et al.
2012/0029278 A1*  2/2012  Sato ................. A61B 17/00234
                                              600/104

FOREIGN PATENT DOCUMENTS

JP    2011-526803 A   10/2011
JP       4801230 B2   10/2011
WO  WO 2010/002457 A1   1/2010

OTHER PUBLICATIONS

International Search Report dated Jul. 19, 2016 issued in PCT/JP2016/062248.
(Continued)

*Primary Examiner* — Elizabeth Houston
*Assistant Examiner* — Mohamed Gabr
(74) *Attorney, Agent, or Firm* — Scully, Scott, Murphy & Presser, P.C.

(57) ABSTRACT

An endoscopic treatment tool set includes: an endoscopic treatment tool that includes a sheath having a lumen, an elongated shaft inserted into the lumen and the elongated shaft having an insertion passage, a stylet disposed in the insertion passage, an implant connected to the stylet, and a manipulation part provided at the sheath; and a jig. The endoscopic treatment tool is packed together with the jig. The jig is coupled to a proximal end portion of the stylet disposed in the manipulation part and the jig is configured to be movable relative to the manipulation part. The implant is connected to the jig via the stylet, and the implant is configured such that the jig is pulled toward a proximal end side of the manipulation part so that the stylet is moved to a proximal end side in the insertion passage and the implant is loaded in the insertion passage.

10 Claims, 24 Drawing Sheets

(51) Int. Cl.
*A61B 17/12* (2006.01)
*A61B 17/064* (2006.01)
*A61B 17/068* (2006.01)
*A61B 17/06* (2006.01)
*A61B 17/29* (2006.01)
*A61B 90/00* (2016.01)

(52) U.S. Cl.
CPC ........... *A61B 17/11* (2013.01); *A61B 17/1114* (2013.01); *A61B 17/1214* (2013.01); *A61B 2017/00323* (2013.01); *A61B 2017/00367* (2013.01); *A61B 2017/00477* (2013.01); *A61B 2017/0645* (2013.01); *A61B 2017/0649* (2013.01); *A61B 2017/06185* (2013.01); *A61B 2017/1205* (2013.01); *A61B 2017/2916* (2013.01); *A61B 2090/034* (2016.02)

(58) Field of Classification Search
CPC .. A61B 2017/1139; A61B 2017/00477; A61B 17/1114; A61B 17/11; A61B 17/00234; A61B 17/0644; A61B 17/3468; A61B 1/018; A61F 2002/041; A61F 2002/044; A61F 2/88
See application file for complete search history.

(56) References Cited

OTHER PUBLICATIONS

Japanese Office Action dated Feb. 7, 2017 issued in Japanese Patent Application No. 2016-567056.

\* cited by examiner

ENDOSCOPIC TREATMENT TOOL SET

This application is a continuation application based on PCT Patent Application No. PCT/JP2016/062248, filed Apr. 18, 2016, whose priority is claimed on Japanese Patent Application No. 2015-184394, filed Sep. 17, 2015. The contents of both the PCT Patent Application and the Japanese Patent Application are incorporated herein by reference.

BACKGROUND OF THE INVENTION

Field of the Invention

The present invention relates to an endoscopic treatment tool set.

Description of Related Art

Conventionally, a method of indwelling a clip-like implant in a luminal tissue or the like to anastomose the luminal tissue has been known. For example, Japanese Patent No. 4801230 discloses an applicator which indwells a coil spring-like implant in a living tissue and a method for indwelling an implant.

A tissue-fastening tool (an implant) disclosed in Japanese Patent No. 4801230 is, for example, made of a highly elastic metal wire material, has a coil shape in a natural state, and is configured to be elastically deformable to be extended in a longitudinal direction by an external force. In the applicator and the method for indwelling the implant disclosed in Japanese Patent No. 4801230, a tissue-fastening tool is inserted as an extended state, in a tubular member having a sharp inclined end surface at a distal end thereof. Next, in a state in which the inclined end surface of the tubular member is extruded from a sheath and penetrates the living tissue and the tubular member penetrates the living tissue, a part of the tissue-fastening tool in the longitudinal direction is extruded from the distal end of the tubular member by a stylet. Thereafter, the tubular member is removed from the tissue, and the remaining part of the tissue-fastening tool is extruded from the tubular member. When the tissue-fastening tool is extruded from the tubular member and indwelled in the tissue, the tissue-fastening tool is restored to a coil shape at a time of being formed to tighten a luminal tissue.

SUMMARY OF THE INVENTION

According to a first aspect of the present invention, an endoscopic treatment tool set includes: an endoscopic treatment tool that includes a sheath in which a lumen extending from a distal end to proximal end of the sheath is formed, an elongated shaft which is inserted into the lumen, the elongated shaft being configured to protrude and retract from the distal end of the sheath, and the elongated shaft including an insertion passage therein, a stylet which is disposed in the insertion passage to be movable relative to the elongated shaft, an implant which includes a proximal end portion connected to a distal end of the stylet in the insertion passage, and a manipulation part which is provided at a proximal end side of the sheath; and a jig that is configured to be connected to a proximal end portion of the stylet. The endoscopic treatment tool is packed together with the jig in a state in which the proximal end portion of the implant is located inside the insertion passage and a distal end portion of the implant is exposed from the elongated shaft. The jig is coupled to the proximal end portion of the stylet disposed in the manipulation part and the jig is configured to be movable relative to the manipulation part. The implant is connected to the jig via the stylet. The implant is configured such that the jig is pulled toward a proximal end side of the manipulation part so that the stylet is moved to a proximal end side in the insertion passage and the implant is loaded in the insertion passage.

According to a second aspect of the present invention, in the endoscopic treatment tool set according to the first aspect, a curved shape may be imparted to the implant in advance, and part of the implant exposed from the elongated shaft may form the curved shape.

According to a third aspect of the present invention, in the endoscopic treatment tool set according to the first aspect, the jig may include a shaft which is configured to be inserted into the manipulation part, a jig side coupling part which is provided at a distal end portion of the shaft and the jig side coupling part being coupled to the proximal end portion of the stylet such that a rotation of the stylet around a longitudinal axis of the stylet and a movement of the shaft in a longitudinal axis of the shaft are linked with each other, and a handle which is provided at a proximal end portion of the shaft and the handle supporting the shaft such that the shaft rotates freely and the shaft being movable toward a proximal end side in the longitudinal axis of the shaft.

DETAILED DESCRIPTION OF THE INVENTION

An endoscopic treatment tool according to an embodiment of the present invention will be described. In the present embodiment, an example of an implant-indwelling device (hereinafter simply referred to as an "indwelling device") will be described as an endoscopic treatment tool.

First, an implant which is loaded in an implant-indwelling device 1 and indwelled in the body will be described. As the implant, it is possible to use a known implant which is made of a highly elastic metal wire material, has a curved shape in advance, is elastically deformable, and has a restoring force restoring the implant to the curved shape. In the present embodiment, as represented in FIG. 1, an example (see FIGS. 20 to 26) is represented in which a tissue-fastening tool 2 that is formed by winding one shape memory wire in a coil shape and that sandwiches and anastomoses two luminal tissues of a tissue D of a duodenum and a tissue CBD of a common bile duct in a close-contact state as represented in FIG. 2 is indwelled as an implant.

The tissue-fastening tool (a treatment part) 2 includes an implant-coupling part (a coupling part) 22 at a proximal end 21 thereof.

Figure 1:
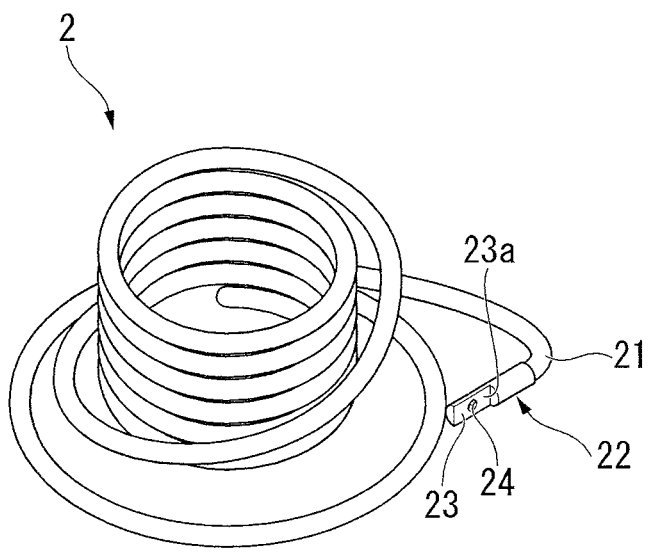
FIG. 1 is a perspective view representing an example of an implant according to an embodiment of the present invention.
Figure 2:
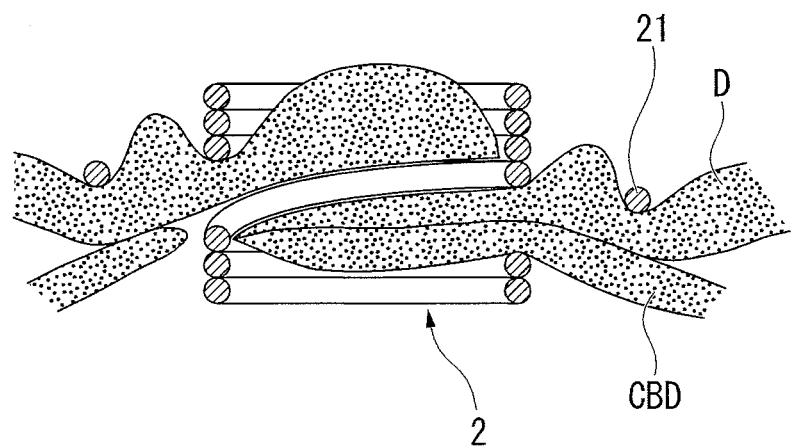
FIG. 2 is a diagram representing an example of a usage mode of the implant of the embodiment of the present invention.

As represented in FIG. 1, the implant-coupling part 22 has a first engagement part main body 23 and a recessed part 24. The first engagement part main body 23 has a semicircular pillar-shaped part obtained by cuffing a cylinder in half along a central axis thereof. The recessed part 24 is a hole formed to extend in a perpendicular direction from a planar part 23a parallel to a longitudinal axis of the first engagement part main body 23. The implant-coupling part 22 is configured to be engageable with a stylet to be described later.

Figure 3:
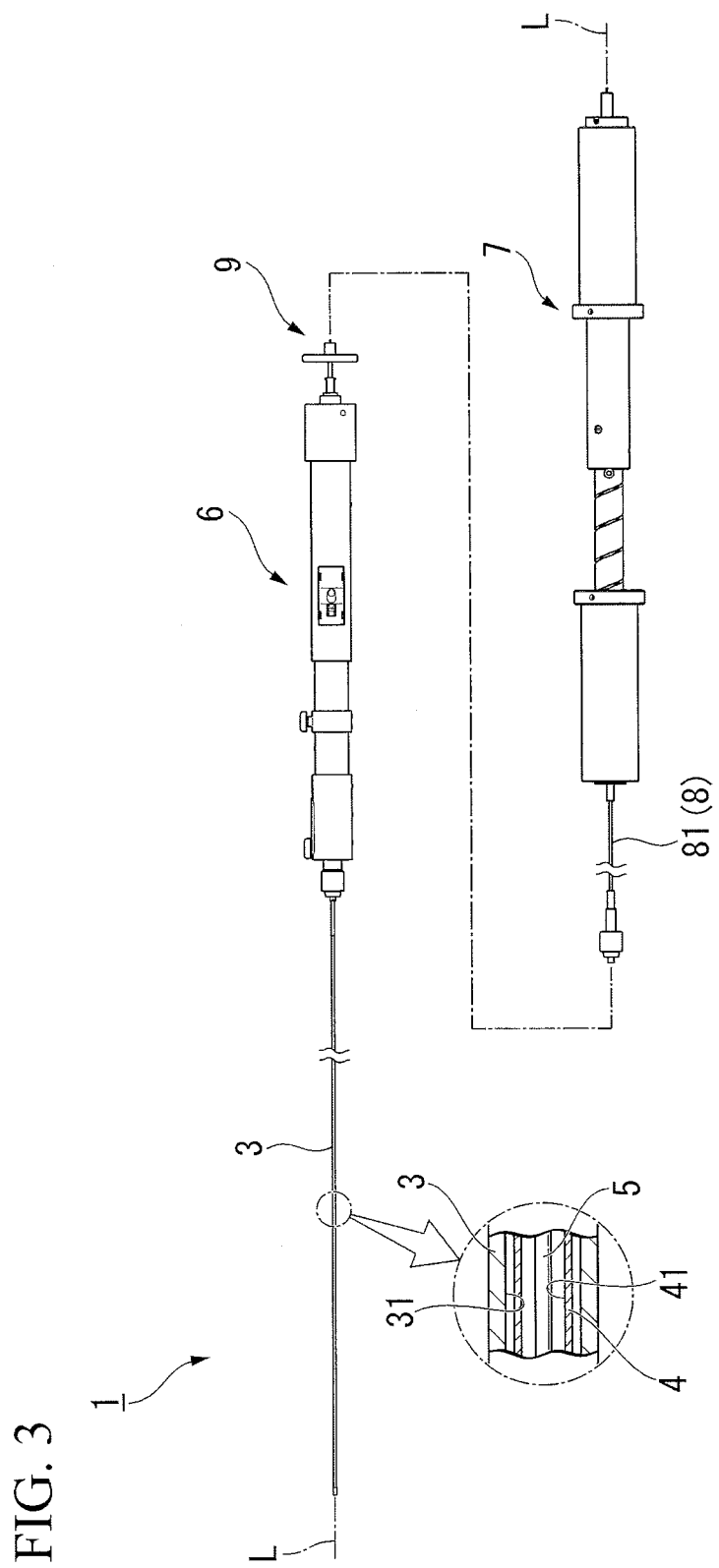
FIG. 3 is an overall diagram representing an endoscopic treatment tool according to the embodiment of the present invention.

FIG. 3 is an overall diagram representing the indwelling device 1 according to this embodiment. The indwelling device 1 is a device for indwelling the tissue-fastening tool 2 in a body using an endoscope. The indwelling device 1 has a sheath 3, a needle tube (an elongated shaft and a treatment part) 4, a stylet (a treatment part) 5, a main manipulation part 6, an auxiliary manipulation part 7, and a manipulation transmission member (hereafter, referred to as a "transmission member" in some cases) 8. The sheath 3, the needle tube 4, the stylet 5, and the main manipulation part 6 are disposed on a central axis L of the sheath 3. The auxiliary manipulation part 7 is coupled to the main manipulation part 6 on the central axis L of the sheath 3. In the following description of the main manipulation part 6 and the auxiliary manipulation part 7, the term "central axis" is used with a meaning including an extension line of the central axis L of the sheath 3 when the main manipulation part 6 and the auxiliary manipulation part 7 are disposed on the central axis L of the sheath 3.

Figure 4:
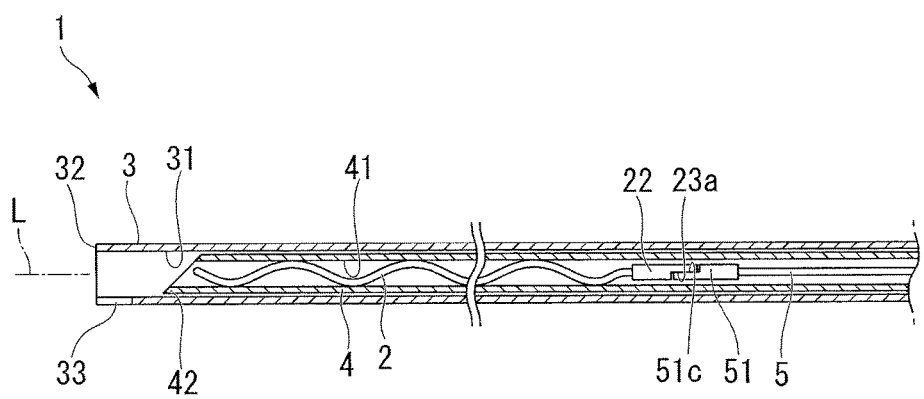
FIG. 4 is a cross-sectional view of a distal end portion of the endoscopic treatment tool according to the embodiment of the present invention.

FIG. 4 is a cross-sectional view of a distal end portion of the indwelling device 1. The sheath 3 is a part which is inserted into a body. As represented in FIGS. 3 and 4, a lumen 31 is formed inside the sheath 3 and extends from a distal end thereof to a proximal end thereof. As represented in FIG. 4, a notched part 33 extending in a direction of the central axis L is formed in a distal end opening portion 32 of the sheath 3. The needle tube 4 to be described later is inserted into the sheath 3 so as to freely advance and retract. A proximal end side of the sheath 3 is connected to the main manipulation part (the manipulation part) 6. The sheath 3 is inserted into a treatment tool channel 102 of an endoscope insertion part 101 (see FIG. 20).

As represented in FIG. 4, the needle tube 4 is a long member having a hollow needle tube insertion passage (an insertion passage) 41. The needle tube 4 is inserted into the lumen 31 to be projectable and retractable from a distal end of the sheath 3. A distal end (a puncturing part) 42 of the needle tube 4 is formed to be sharp and functions as a puncture needle. A proximal end of the needle tube 4 is attached to a distal end of a needle guide 67 (see FIG. 6A), which will be described later, to be relatively rotatable and immovable forward and backward. A superelastic alloy represented by a nickel titanium alloy or stainless steel can be adopted, for example, as a material of the needle tube 4.

The stylet 5 is a long core material, a distal end portion thereof is located inside the needle tube insertion passage 41 (see FIG. 4), and a proximal end portion thereof extends to the main manipulation part 6 provided on the proximal end side of the sheath 3. The stylet 5 is a member which advances and retracts the tissue-fastening tool 2 with respect to the needle tube insertion passage 41. The stylet 5 is configured to be projectable and retractable from the distal end of the sheath 3.

Figure 7:
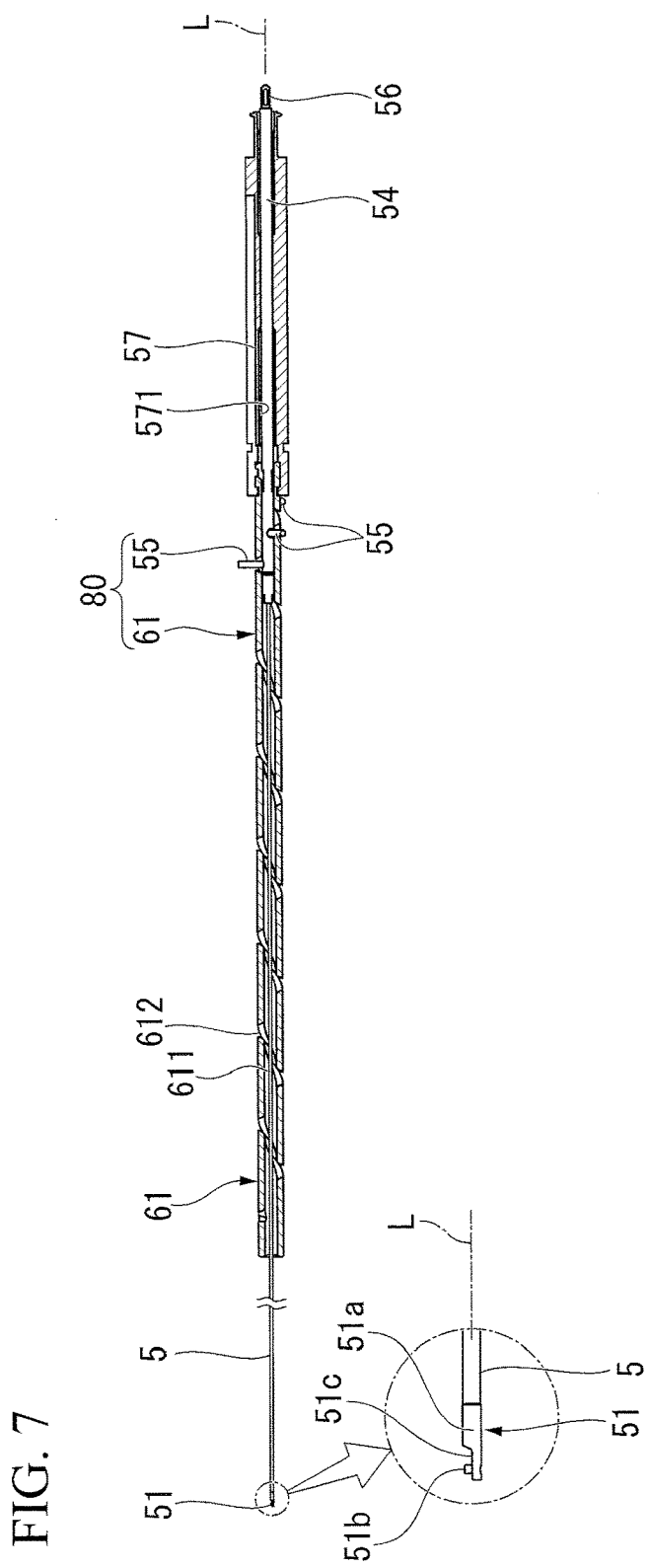
FIG. 7 is a cross-sectional view of a stylet and a first cam tube according to the embodiment of the present invention.

FIG. 7 is a cross-sectional view of the stylet 5 and a first cam tube (a cam tube) 61. As represented in FIG. 7, a distal end engagement part 51 is provided at a distal end portion of the stylet 5. The distal end engagement part 51 has a second engagement part main body 51a and a protruding part 51b. A proximal end portion of the second engagement part main body 51a has a cylindrical shape, and a distal end portion thereof has a semi-cylindrical shape in which a cylinder is cut in half on the central axis L. The protruding part 51b is formed to protrude in a perpendicular direction from a planar part 51c of the second engagement part main body 51a parallel to the central axis L. As represented in FIG. 4, when the planar parts 23a and 51c come into contact with each other inside the needle tube 4 and the protruding part 51b is inserted into the recessed part 24, the distal end engagement part 51 and the implant-coupling part 22 engage with each other and the tissue-fastening tool 2 is coupled to the stylet 5.

As represented in FIG. 7, a stylet proximal end member 54 is fixed to the proximal end portion of the stylet 5. Three first engaging pins (cam followers and first projections) 55 are provided at a distal end portion of the stylet proximal end member 54 to protrude in a direction orthogonal to the central axis L. The three first engaging pins 55 are provided to be spaced part at an equal angle in a circumferential direction and spaced apart at an equal interval in the direction of the central axis L.

Figure 6A:
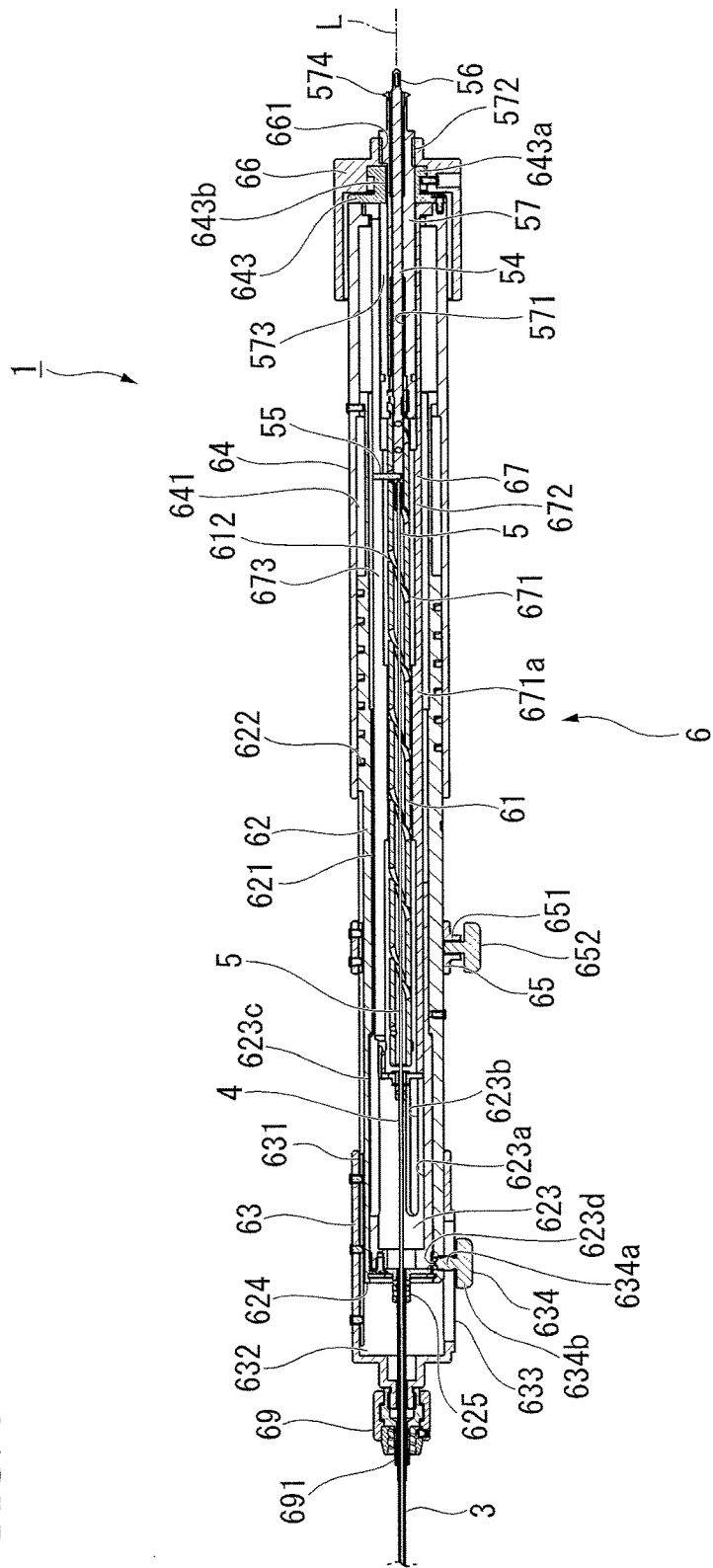
FIG. 6A is a cross-sectional view of the main manipulation part according to the embodiment of the present invention.
Figure 6B:
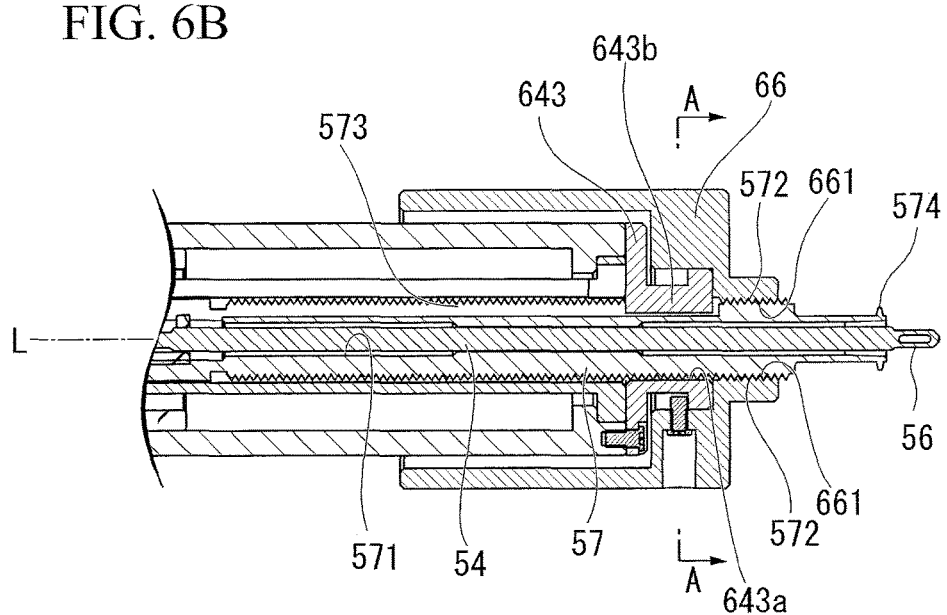
FIG. 6B is a cross-sectional view of a proximal end portion of the main manipulation part according to the embodiment of the present invention.
Figure 8:
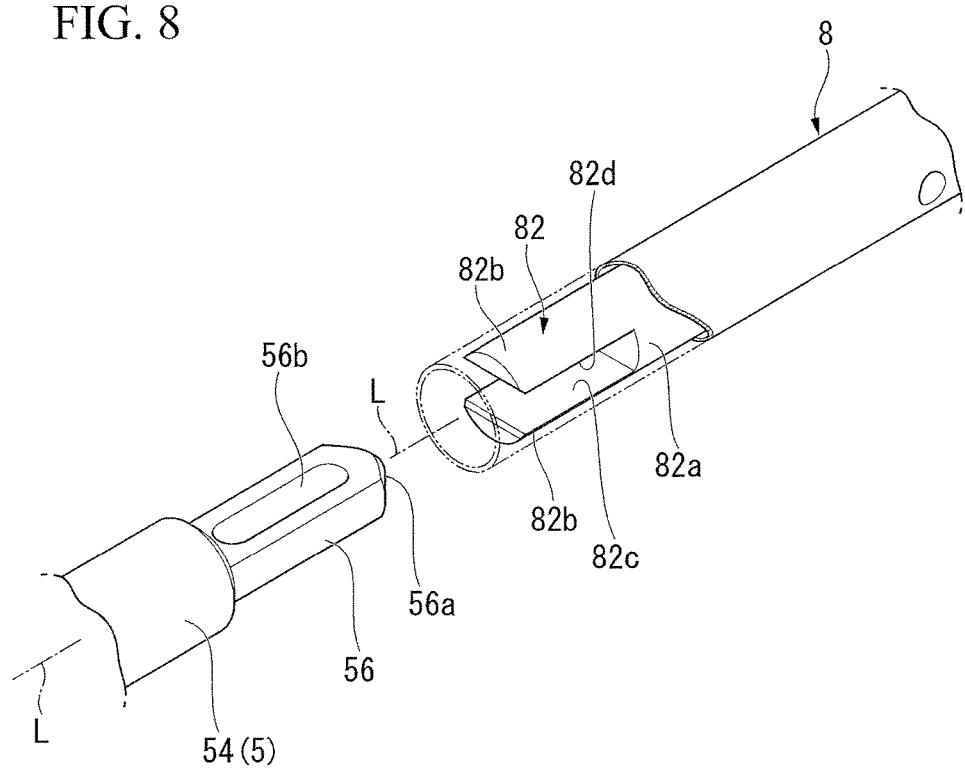
FIG. 8 is a perspective view of a proximal end portion of the stylet and a distal end portion of a manipulation transmission member according to the embodiment of the present invention.

FIG. 6A is a cross-sectional view of the main manipulation part 6. FIG. 6B is a cross-sectional view of a proximal end portion of the main manipulation part 6. As represented in FIGS. 6A, 6B, and 7, the stylet proximal end member 54 is inserted through a lumen 571 of a Luer joint 57. FIG. 8 is a perspective view of the proximal end portion of the stylet 5 and a distal end portion of the transmission member 8. A proximal end engagement part 56 is provided on the stylet proximal end member 54. The proximal end engagement part 56 is an engagement member that engages with the distal end portion of the transmission member 8. As represented in FIG. 8, the proximal end engagement part 56 has a substantially flat plate shape and is provided to extend along the central axis L from a proximal end of the stylet proximal end member 54. A proximal end portion 56a of the proximal end engagement part 56 has a surface which protrudes toward a proximal end side. A through-hole 56b is formed in the proximal end engagement part 56.

The proximal end engagement part 56 has a size such that the proximal end engagement part 56 is located inside a maximum outer diameter part of the stylet 5 when viewed from the direction of the central axis L.

As represented in FIG. 4, the stylet 5 and the needle tube 4 are inserted through the lumen 31 of the sheath 3 so as to be coaxial with the central axis L of the sheath 3. The sheath 3, the needle tube 4, and the stylet 5 are members that are inserted into a body from a distal end side, and are made of materials that are elastically deformable along with bending of the treatment tool channel 102 when inserted through the treatment tool channel 102 of the endoscope 100.

Figure 5:
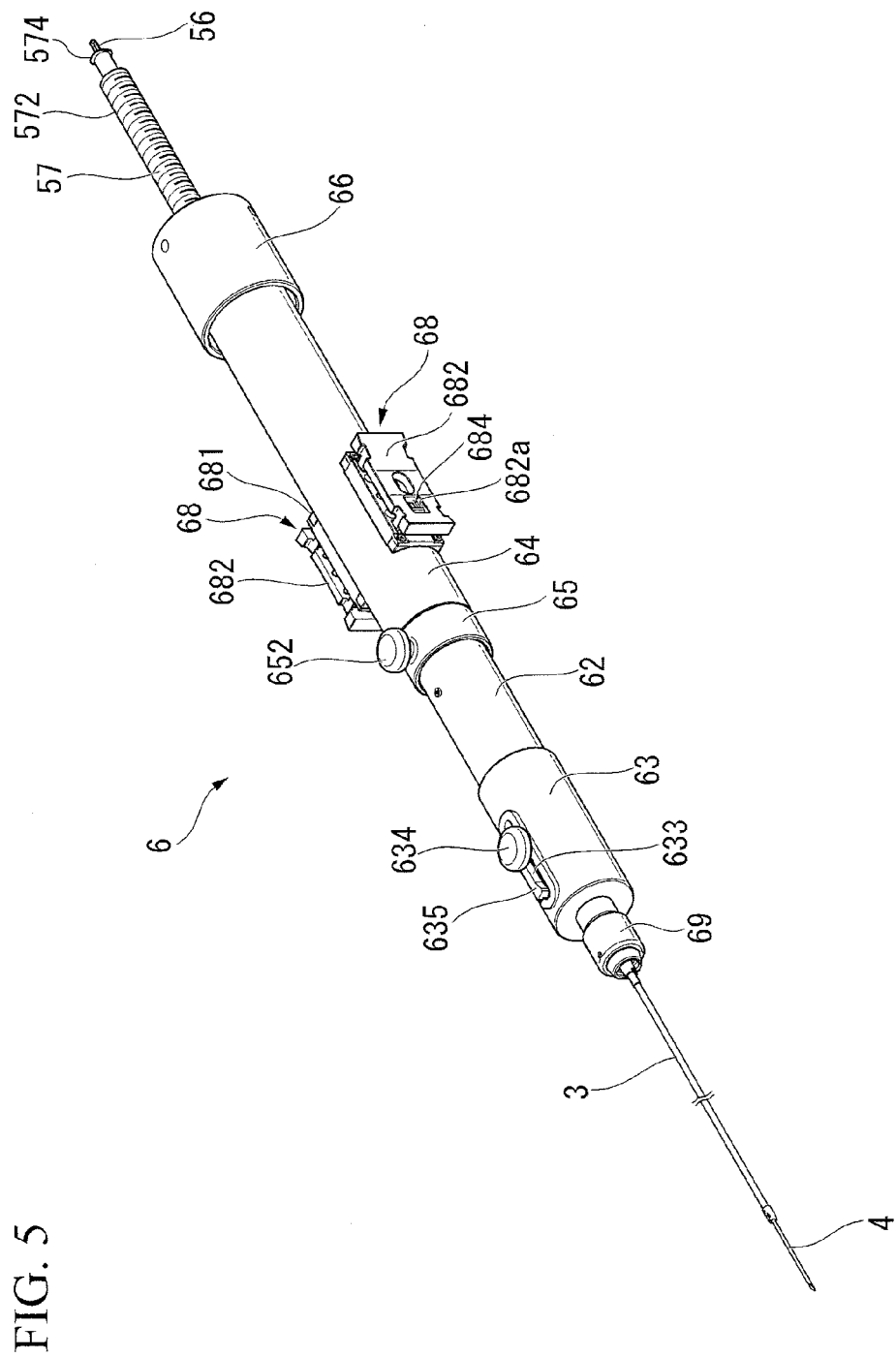
FIG. 5 is a perspective view of a main manipulation part according to the embodiment of the present invention.
Figure 6C:
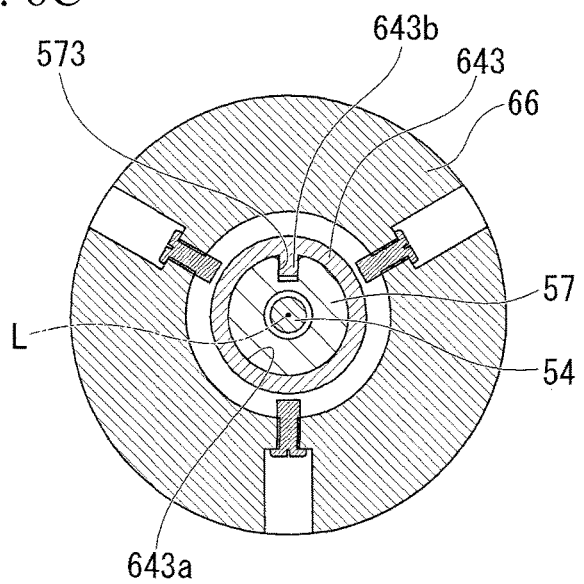
FIG. 6C is a cross-sectional view taken along line A-A in FIG. 6B.

The main manipulation part 6 is provided along the central axis L of the sheath 3 on the proximal end side of the sheath 3. FIG. 5 is a perspective view of the main manipulation part 6. FIG. 6C is a cross-sectional view taken along line A-A in FIG. 6B. FIG. 3 represents the main manipulation part 6 in a state in which a jig 9 to be described later is mounted thereon. FIGS. 5, 6A, 6B, and 6C illustrate the main manipulation part 6 from which the jig 9 is removed. The main manipulation part 6 is provided to operate the sheath 3, the needle tube 4, and the stylet 5. The main manipulation part 6 includes the first cam tube 61, a main manipulation part main body 62, a sheath slider 63, a needle slider (a slider unit and an elongated shaft manipulation part) 64, a needle slider stopper 65, a first rotation knob (an elongated shaft manipulation part) 66, the needle guide 67, and a mounting part 69.

As represented in FIG. 7, the first cam tube 61 is a tube in which a first insertion passage 611 extending along the central axis L and a first guide passage (a cam and a guide passage) 612 are formed. The first guide passage 612 communicates with an inside and outside of a tube and is formed in a spiral shape. The spiral shape of the first guide passage 612 is formed such that the first engaging pin 55 advances from a proximal end of the first guide passage 612 to a distal end thereof while rotating clockwise when viewed from the proximal end toward the distal end.

Figure 9:
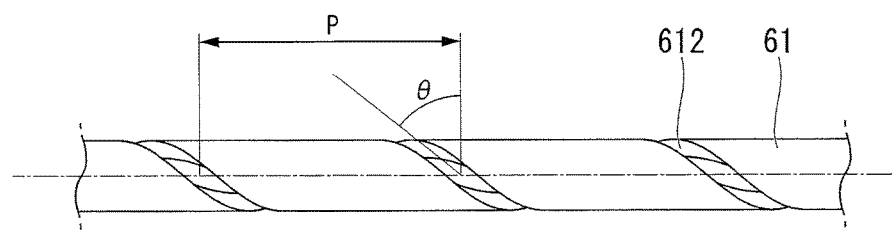
FIG. 9 is a schematic view representing a first guide passage of the first cam tube according to the embodiment of the present invention.

FIG. 9 is a schematic view representing the spiral shape of the first guide passage 612. As represented in FIG. 9, the spiral shape of the first guide passage 612 is formed at a constant pitch. A spiral pitch P of the spiral shape of the first guide passage 612 is formed at a pitch which is equal to a length obtained by dividing a length of the wire material of a coil in a part of the tissue-fastening tool 2 indwelled in a luminal organ on a proximal side by the number of turns of the coil of that part. Further, the number of turns of the spiral shape of the first guide passage 612 is set to be greater than or equal to the number of turns of a partial coil that is indwelled in the luminal organ on the proximal side of the tissue-fastening tool 2. Furthermore, a lead angle θ of the first guide passage 612 is set within a range of 20 degrees or more to 75 degrees or less.

As represented in FIGS. 6A and 7, the proximal end portion of the stylet 5 and the stylet proximal end member 54 are inserted into the first cam tube 61. The first cam tube 61 and the three first engaging pins 55 of the stylet proximal end member 54 constitute a first spiral mechanism 80. The three first engaging pins 55 of the stylet proximal end member 54 are inserted into the first guide passage 612 to protrude outward from the first insertion passage 611. By the engagement between the three first engaging pins 55 and the first guide passage 612, the stylet 5 and the stylet proximal end member 54 are configured to be supported by the first cam tube 61 and to advance and retract while rotating with respect to the first cam tube 61. In this way, the spiral mechanism defines the motion of the stylet 5.

A proximal end portion of the first cam tube 61 and a distal end portion of the Luer joint 57 are fixed to each other. The Luer joint 57 and the stylet 5 are configured to be relatively rotatable. The stylet 5 and the stylet proximal end member 54 can advance and retract in the direction of the central axis L while rotating with respect to the first cam tube 61 and the Luer joint 57.

Figure 6D:
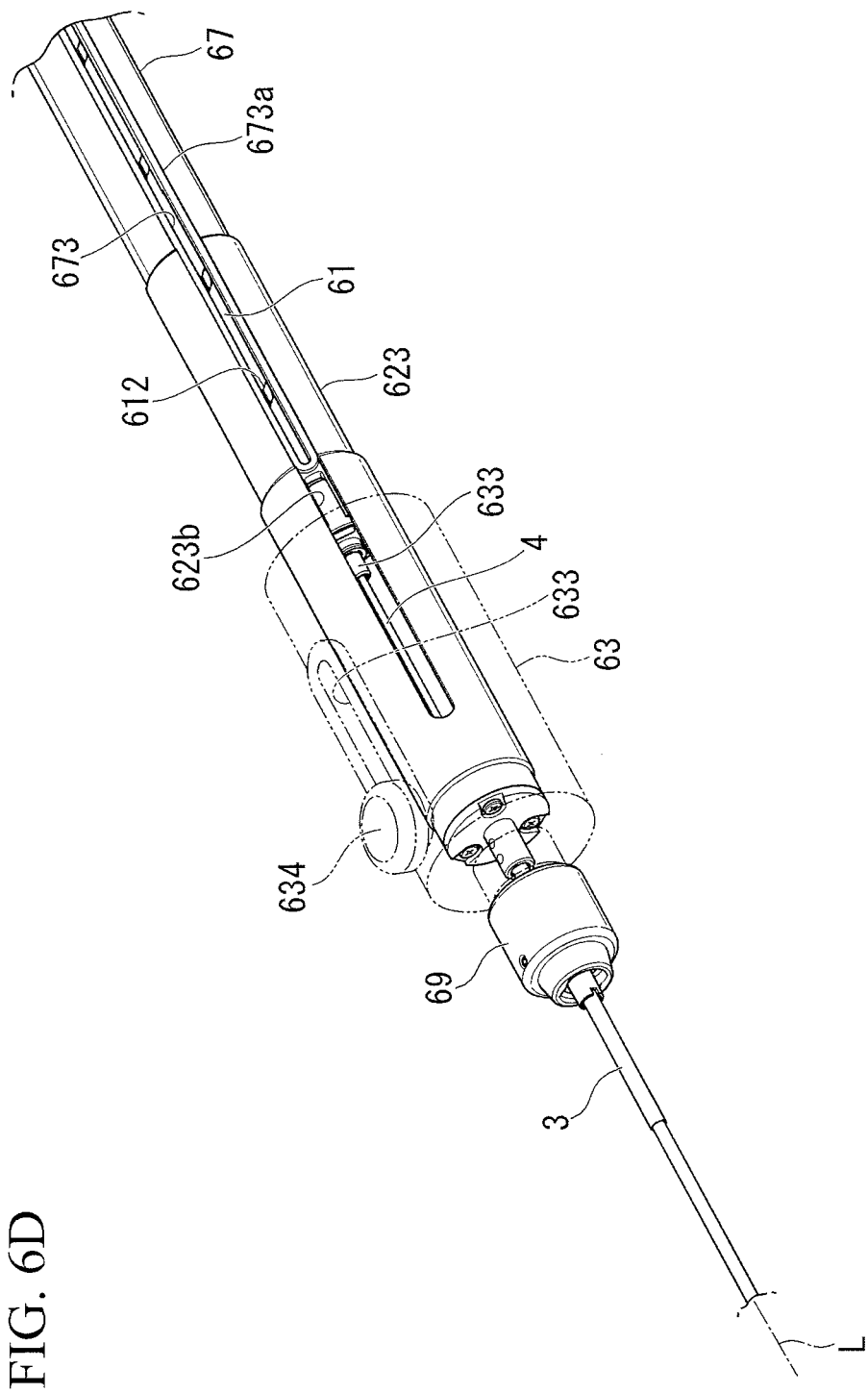
FIG. 6D is a perspective view representing a state in which a needle guide is inserted into a sheath guide according to the embodiment of the present invention.
Figure 10:
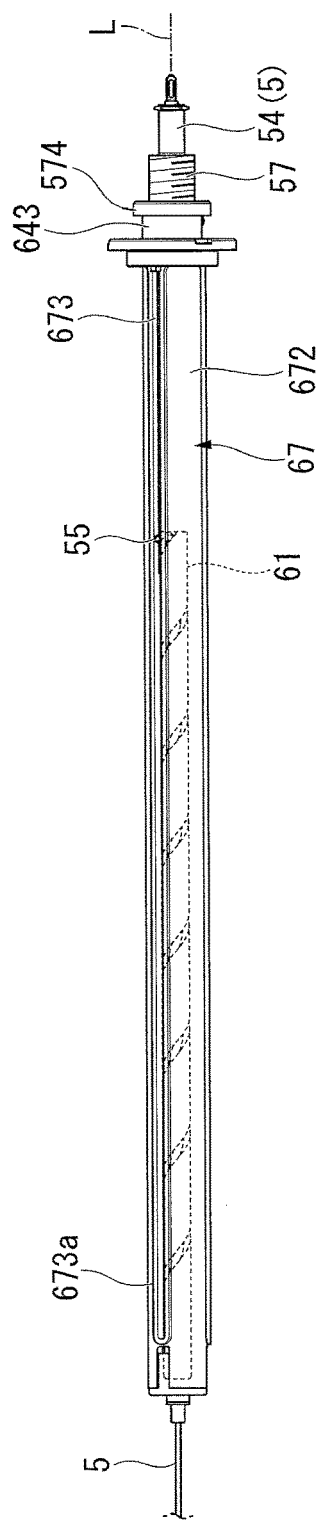
FIG. 10 is a side view representing a state in which the stylet and a stylet proximal end member are inserted into the needle guide according to the embodiment of the present invention.

FIG. 10 is a side view representing a state in which the first cam tube 61, the stylet 5, and the stylet proximal end portion are inserted into the needle guide 67. FIG. 6D is a perspective view representing a state in which the needle guide 67 is inserted into a sheath guide 623. As represented in FIG. 10, the needle guide 67 has a substantially cylindrical shape, and as represented in FIG. 6A, has a needle guide insertion passage 671 which extends in the direction of the central axis L. As represented in FIGS. 6D and 10, on a side wall part 672 of the needle guide 67, a guide slit 673 communicating the outside of the needle guide 67 and the inside of the needle guide insertion passage 671 is formed along the direction of the central axis L. Three guide slits 673 are formed at equal intervals in a circumferential direction of the needle guide 67.

As represented in FIG. 6A, the needle guide insertion passage 671 is formed with a small-diameter part 671a having a small opening diameter of the needle guide insertion passage 671 in a partial region in the direction of the central axis L. The opening diameter of the small-diameter part 671a is set to be slightly larger than an outer diameter of the first cam tube 61.

The needle slider end member 643 is fixed to a proximal end of the needle slider 64. The needle guide 67 is sandwiched between the needle slider 64 and the needle slider end member 643 at a proximal end portion, and is supported to be capable of only rotating with respect to the needle slider 64.

The stylet 5, the stylet proximal end member 54, the first cam tube 61, and the Luer joint 57 are inserted into the needle guide insertion passage 671 to be advanceable and retractable with respect to the needle guide 67. When the first cam tube 61 is inserted through the small-diameter part 671a of the needle guide 67, the first cam tube 61 is supported to be relatively advanceable, retractable, and rotatable on the central axis L inside the needle guide insertion passage 671.

As represented in FIG. 10, the three first engaging pins 55 of the stylet proximal end member 54 are respectively engaged with the guide slits 673. The first engaging pin 55 is slidable inside the guide slit 673. That is, the first engaging pin 55 is slidable inside the first guide passage 612 and inside the guide slit 673.

The first cam tube 61 is supported to be capable of only advancing and retracting with respect to the needle slider 64. The first engaging pin 55 of the stylet proximal end member 54 is simultaneously engaged with the first guide passage 612 and the guide slit 673. In other words, the first spiral mechanism 80 including the first cam tube 61 and the first engaging pin 55 is supported by the needle slider 64 and is engaged with the guide slit 673. When the stylet 5 and the stylet proximal end member 54 rotate around the central axis L, the stylet 5 and the stylet proximal end member 54 advance and retract with respect to the needle slider 64 while rotating, and the needle guide 67 is configured to only rotate. In this description, a motion in which the stylet 5 advances while rotating is referred to as a "spiral motion" in some cases.

As represented in FIG. 5, the main manipulation part main body 62 has a substantially cylindrical shape, and as represented in FIG. 6A, a second insertion passage 621 extending in the direction of the central axis L is formed in the main manipulation part main body 62. A sheath guide 623 is inserted into a distal end side of the second insertion passage 621. The sheath guide 623 is rotatably supported with respect to the main manipulation part main body 62 near a distal end of the second insertion passage 621. A sheath fixing part 625 is fixed to a distal end portion of the sheath guide 623, and the proximal end of the sheath 3 is fixed to the sheath fixing part 625.

As represented in FIG. 6D, the sheath guide 623 is a substantially cylindrical member extending in the direction of the central axis L, and as represented in FIG. 6A, a third insertion passage 623a is formed therein. The stylet 5 inserted through the needle guide 67 and the first cam tube 61 is inserted through the third insertion passage 623a to be advanceable and retractable. In the sheath guide 623, first slits 623b extending in the direction of the central axis L are formed at three positions at equal intervals in the circumferential direction. The first slits 623b are engaged with ribs 673a (see FIG. 10) formed on the radial outside of the circumference of the guide slit 673 of the needle guide 67. Therefore, when the needle guide 67 rotates around the central axis L, the sheath guide 623 rotates to follow the rotation. However, even if the needle guide 67 advances and retracts in the direction of the central axis L, the sheath guide 623 does not follow the movement. From the above, the first spiral mechanism 80 rotates the sheath 3 around the central axis L due to the engagement between the cam and the cam follower.

The ring-shaped needle slider stopper 65 is externally mounted on the main manipulation part main body 62. The needle slider stopper 65 has an inner diameter that enables the needle slider stopper 65 to advance and retract in the direction of the central axis L with respect to the main manipulation part main body 62. A screw hole 651 is formed on the needle slider stopper 65. A needle stopper screw 652 is screwed into the screw hole 651. When the needle stopper screw 652 is inserted and screwed into the screw hole 651, a distal end of the needle stopper screw 652 presses an outer peripheral surface of the main manipulation part main body 62 and a position of the needle slider stopper 65 with respect to the main manipulation part main body 62 is fixed.

Figure 11:
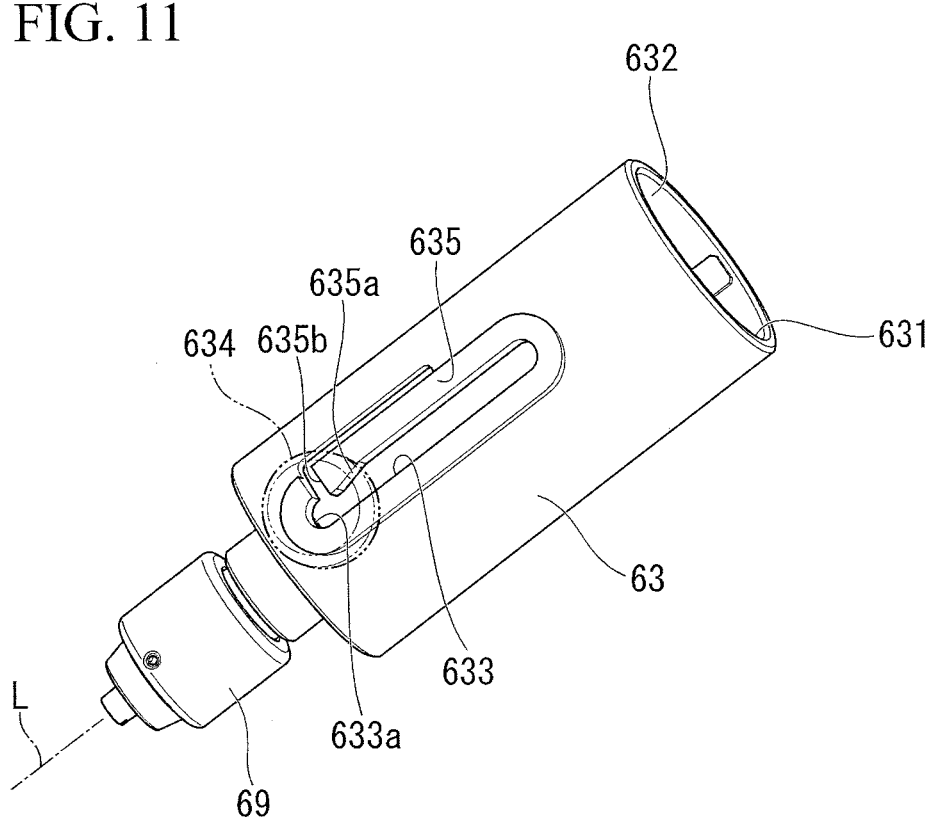
FIG. 11 is a perspective view of a sheath slider according to the embodiment of the present invention.

The sheath slider 63 is provided on a distal end side of the main manipulation part main body 62. As represented in FIGS. 5 and 11, the sheath slider 63 is a cylindrical member, and a fourth insertion passage 632 extending in the direction of the central axis L from a proximal end opening 631 is formed thereon. A distal end portion of the main manipulation part main body 62 is inserted into the proximal end opening 631. The main manipulation part main body 62 is provided to be advanceable and retractable inside the fourth insertion passage 632.

The mounting part 69 is fixed to a distal end of the sheath slider 63. The mounting part 69 is fixed to a manipulation part 104 of the endoscope 100 by being screw-engaged with a port 103 of the treatment tool channel 102 of the endoscope 100 (see FIG. 19). The main manipulation part 6 is fixed to the endoscope 100 by the mounting part 69. A distal end insertion passage 691 extending in the direction of the central axis L is formed in the mounting part 69. The sheath 3 is inserted through the distal end insertion passage 691 to be advanceable and retractable. The sheath 3 can be advanced and retracted by moving the main manipulation part main body 62 to advance and retract in a linear direction with respect to the sheath slider 63.

A second slit 633 extending in the direction of the central axis L is formed in the sheath slider 63. A fixing knob 634 is inserted into the second slit 633 from an outer peripheral side thereof. A screw part 634a of the fixing knob 634 passes through the second slit 633 and protrudes toward a side of the fourth insertion passage 632 of the sheath slider 63. A distal end of the screw part 634a of the fixing knob 634 is inserted into a screw hole 623d formed on an outer periphery of the distal end portion of the main manipulation part main body 62. A length of the screw part 634a is set such that a screw head 634b of the fixing knob 634 can be slightly separated from the second slit 633 while maintaining a state in which a part of a distal end side of the screw part 634a is screwed into the screw hole of the main manipulation part main body 62.

When the screw part 634a is screwed into a side of the main manipulation part main body 62, the sheath slider 63 around the second slit 633 is clamped by the screw head 634b and the main manipulation part main body 62. As a result, a positional relationship between the sheath slider 63 and the main manipulation part main body 62 in the direction of the central axis L is fixed. When screwing of the screw part 634a is loosened, the main manipulation part main body 62 is in a state that is capable of advancing and retracting in the linear direction with respect to the sheath slider 63. That is, relative positions of the main manipulation part main body 62 to the sheath slider 63 can be switched into a fixed state or a relatively movable state due to the second slit 633 and the fixing knob 634.

Depending on a position of the fixing knob 634 with respect to the second slit 633, an amount of protrusion of the sheath 3 from the main manipulation part 6 (an amount of protrusion from the mounting part 69) is determined. A length of the second slit 633 in the direction of the central axis L corresponds to an advancement and retraction movement length of the sheath 3. When the fixing knob 634 is disposed at a position at which it comes into contact with a distal end of the second slit 633, the amount of protrusion of the sheath 3 from a distal end of the main manipulation part 6 (the amount of protrusion from the mounting part 69) is maximized. Meanwhile, when the fixing knob 634 is disposed at a position at which it comes into contact with a proximal end of the second slit 633, the sheath 3 is disposed at a maximally retracted position, and the amount of protrusion of the sheath 3 from the distal end of the main manipulation part 6 is minimized.

As represented in FIGS. 5 and 11, a resin spring 635 configured of a cantilever extending in the direction of the central axis L is provided in a part of the second slit 633 of the sheath slider 63. As represented in FIG. 11, the resin spring 635 is provided with an inclined surface 635a and a locking surface 635b. When the fixing knob 634 is advanced to a distal end side in the direction of the central axis L, the screw part 634a comes in contact with the inclined surface 635a and advances while gradually pressing the resin spring 635, and comes into contact with the distal end 633a of the second slit 633. The screw part 634a is disengaged from the inclined surface 635a when coming into contact with the distal end 633a of the second slit 633, and the resin spring 635 returns to an original position thereof. Even if a force returning the fixing knob 634 to a proximal end side in the direction of the central axis L acts in this state, because the screw part 634a hits the locking surface 635b, the screw part 634a does not return because the screw part 634a comes into contact with the locking surface 635b. As described above, even if the screw part 634a is not screwed into the main manipulation part main body 62, the sheath slider 63 can be fixed while the amount of protrusion of the sheath 3 from the main manipulation part 6 is maximized.

As represented in FIGS. 5 and 6A, the needle slider 64 has a substantially cylindrical shape and is provided along the central axis L in an intermediate part of the main manipulation part 6 in the direction of the central axis L. In a fifth insertion passage 641 formed in the needle slider 64, the stylet 5, the first cam tube 61, the needle guide 67, and the main manipulation part main body 62 are sequentially coaxially disposed from a side of the central axis L toward the outside in the radial direction. The first rotation knob 66, which will be described later, is disposed at a proximal end portion of the needle slider 64.

Figure 12:
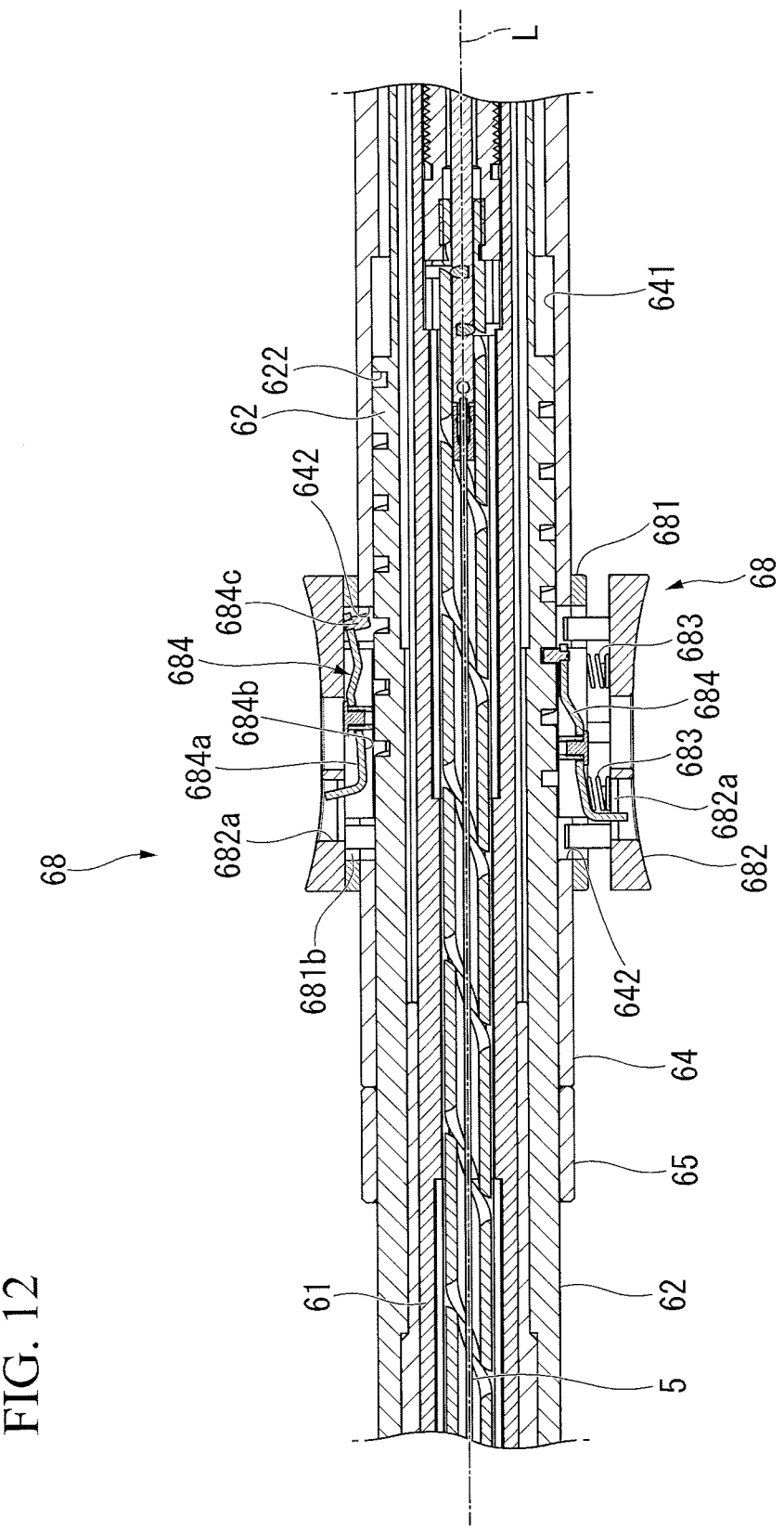
FIG. 12 is a partial cross-sectional view of the main manipulation part according to the embodiment of the present invention.

As represented in FIG. 12, a pair of side holes 642 are formed in the needle slider 64 such that they are opposed to each other in the radial direction. As represented in FIGS. 5 and 12, a slide button unit 68 is provided in each of the pair of side holes 642. The slide button unit 68 is provided to switch between a state in which the needle slider 64 can advance and retract in the direction of the central axis L with respect to the main manipulation part main body 62 and a state in which the needle slider 64 can advance and retract while rotating around the central axis L. The upper side of FIG. 12 represents the slide button unit 68 in a state in which the needle slider 64 can advance and retract in the direction of the central axis L with respect to the main manipulation part main body 62, and the lower side of FIG. 12 represents the slide button unit 68 in a state in which the needle slider 64 can advance and retract while rotating around the central axis L with respect to the main manipulation part main body 62. Actually, the pair of slide button units 68 is switched to one of a state represented on the upper side of FIG. 12 or a state represented on the lower side of FIG. 12.

A base body 681 of the slide button unit 68 is fitted into the side hole 642 and fixed to the needle slider 64, and a button main body 682 is attached to the radial outside of the base body 681. A spring member 683 is provided as a biasing member between the button main body 682 and the base body 681. The button main body 682 is biased in a direction away from the base body 681 toward the outer side in the radial direction by the spring member 683.

The slide button unit 68 further includes a plate 684 between the button main body 682 and the base body 681. The plate 684 is disposed to extend in the direction of the central axis L, and a substantially intermediate part of the plate 684 in the direction of the central axis L is fixed to the base body 681. A hole 681b formed along the central axis L is formed in the base body 681. A distal end portion of the plate 684 is engaged with the slit 682a of the button main body 682, and a proximal end portion of the plate 684 is disposed in the hole 681b of the base body 681. A first surface 684a of the plate 684 faces the button main body 682, and a second surface 684b is located in the hole 681b and disposed to face the main manipulation part main body 62. A locking pin 684c is provided at the proximal end portion of the plate 684 to protrude from the second surface 684b in a thickness direction of the plate 684. A spiral groove 622 is formed on an outer peripheral surface of an intermediate region of the main manipulation part main body 62 in the direction of the central axis L, and the locking pin 684c is switched between a state of being engaged with the spiral groove 622 and a state of not being engaged with the spiral groove 622 as represented in FIG. 12.

When an operator pushes the button main body 682 inward in the radial direction and pushes the button main body 682 until it comes into contact with the base body 681, the distal end portion of the plate 684 is pressed toward the side of the main manipulation part main body 62. Accordingly, the proximal end portion of the plate 684 moves in a direction away from the main manipulation part main body 62 and the locking pin 684c is detached from the spiral groove 622. In this state, because a connection relationship between the needle slider 64 and the main manipulation part main body 62 is released, the needle slider 64 is configured to be advanceable and retractable in the direction of the central axis L with respect to the main manipulation part main body 62.

In a state in which the spring member 683 biases the button main body 682 outward in the radial direction and the button main body 682 is separated from the base body 681, the button main body 682 pulls the distal end portion of the plate 684 outward in the radial direction and the proximal end portion of the plate 684 is biased toward the side of the main manipulation part main body 62. At this time, the locking pin 684c is fitted into the spiral groove 622 formed on the outer peripheral surface of the main manipulation part main body 62. In this state, the needle slider 64 is configured to be advanceable and retractable while rotating with respect to the main manipulation part main body 62.

The first rotation knob 66 is a member that is rotationally manipulated by the operator when sending the tissue-fastening tool 2 from the distal end of the needle tube 4. As represented in FIGS. 5, 6A, 6B, and 6C, the first rotation knob 66 is a cylindrical member and is attached to cover a side surface and a proximal end side of the needle slider end member 643. The first rotation knob 66 is rotatably attached to the needle slider end member 643. A female screw 661 is formed at the center of the first rotation knob 66, and is engaged with a male screw 572 which is cut around an outer periphery of the Luer joint 57. An engaging projection 643b that protrudes in the radial direction is formed in a through-hole 643a which is a substantial center of the needle slider end member 643. A linear groove 573 extending in the direction of the central axis L is formed on the outer periphery of the Luer joint 57. The engaging projection 643b is engaged with the linear groove 573. With this configuration, the Luer joint 57 and the first cam tube 61 fixed to the Luer joint 57 are advanced and retracted with respect to the first rotation knob 66 by the first rotation knob 66 being rotated. At the same time, the stylet 5 engaged with the first cam tube 61 is advanced and retracted with respect to the first rotation knob 66.

Figure 13:
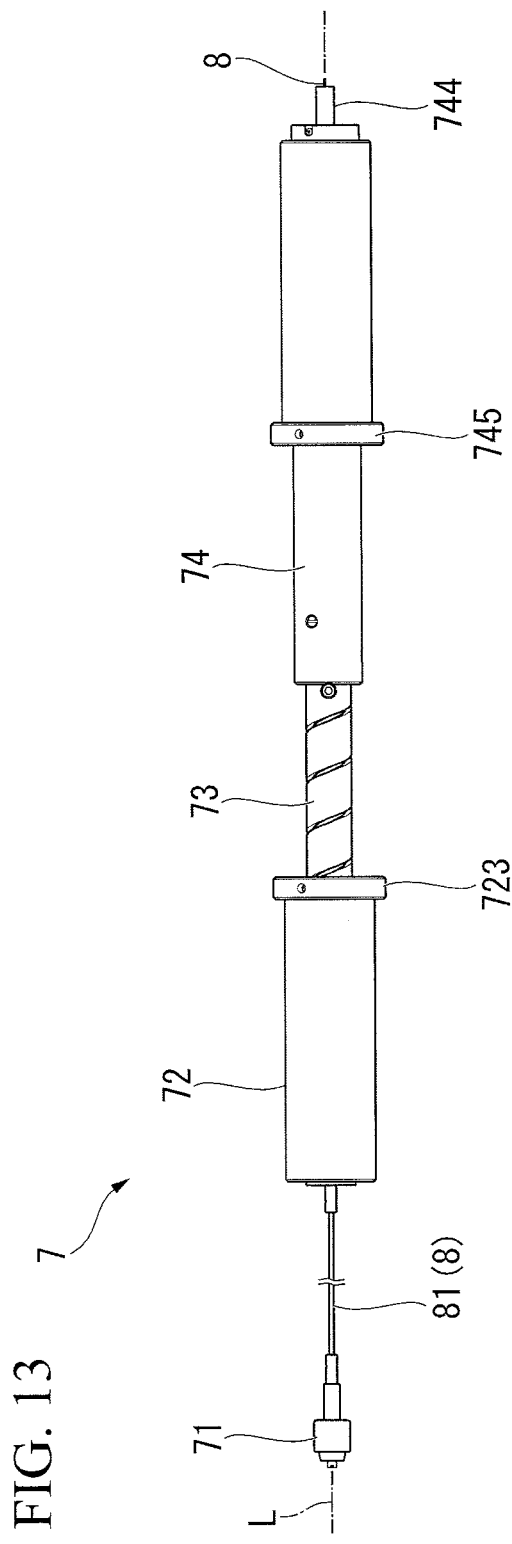
FIG. 13 is a side view of an auxiliary manipulation part according to the embodiment of the present invention.

FIG. 13 is a side view of the auxiliary manipulation part 7 when viewed from a direction orthogonal to the central axis L. The auxiliary manipulation part 7 is disposed to be separated from the main manipulation part 6 and is connected to the main manipulation part 6 via the transmission member 8. The main manipulation part 6 and the auxiliary manipulation part 7 are configured to be separably connected via the transmission member 8. The auxiliary manipulation part 7 advances and retracts the transmission member 8 to manipulate the movement of the stylet 5 within the main manipulation part 6. The auxiliary manipulation part 7 includes a manipulation coupling part 71, an auxiliary manipulation part main body 72, a second cam tube 73, and a rotation handle 74 in order from a distal end side thereof, and the transmission member 8 is inserted throughout the entire length in the direction of the central axis L.

Figure 14A:
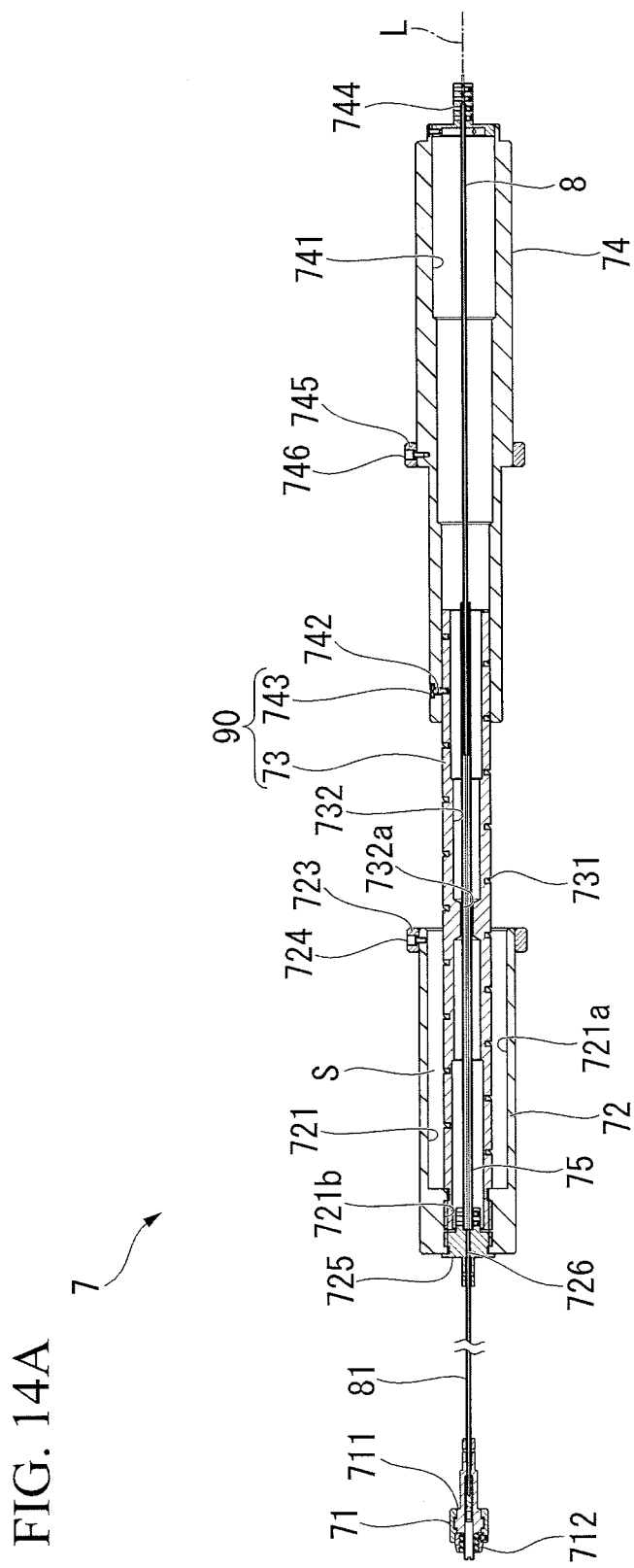
FIG. 14A is a cross-sectional view of the auxiliary manipulation part according to the embodiment of the present invention.
Figure 14B:
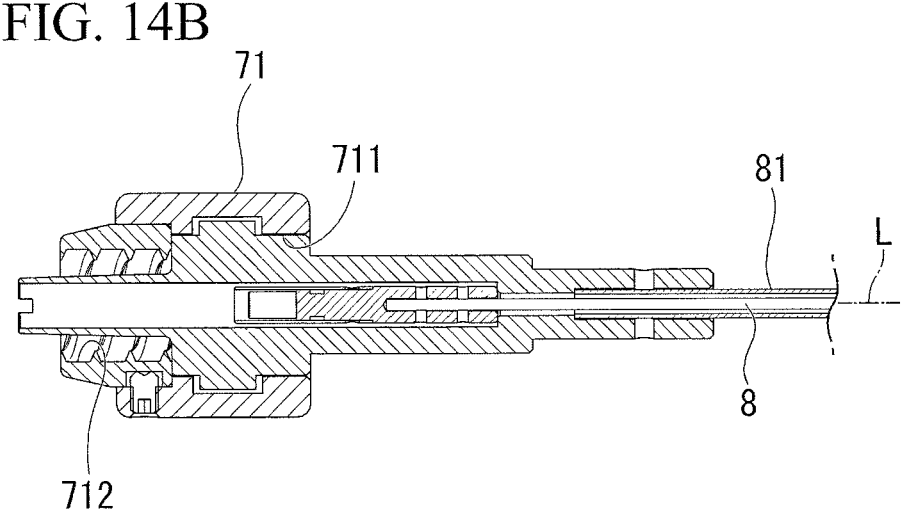
FIG. 14B is a cross-sectional view of a manipulation connection part according to the embodiment of the present invention.

FIG. 14A is a cross-sectional view of the auxiliary manipulation part 7 in a plane passing through the central axis L. FIG. 14B is a cross-sectional view of the manipulation coupling part 71. The manipulation coupling part 71 is a member that is connected to the proximal end portion of the main manipulation part 6 and couples the proximal end portion of the stylet 5 and the distal end portion of the transmission member 8. A sixth insertion passage 711 extending in the direction of the central axis L is formed in the manipulation coupling part 71. A screw groove 712 capable of being screwed to a flange 574 of the Luer joint 57 (see FIG. 5) is formed around the central axis L on an inner peripheral surface of a distal end portion of the sixth insertion passage 711.

The transmission member 8 is a long and flexible core material (a flexible member). A distal end side from a substantially central part of the transmission member 8 in the direction of the central axis L is inserted into a cable tube 81 having flexibility. The transmission member 8 is a transmission member that transmits a manipulation input of the auxiliary manipulation part 7 on the rotation handle 74 to the main manipulation part 6.

As represented in FIG. 8, a stylet engagement part 82 is provided at the distal end of the transmission member 8. The stylet engagement part 82 has two arms 82b extending in parallel with the direction of the central axis L from a base part 82a having a substantially columnar outer shape. The two arms 82b have planar parts 82c and 82d that face each other across the central axis L. A separation distance between the planar parts 82c and 82d in the radial direction (a direction orthogonal to the central axis L) is set to be slightly larger than a plate thickness of the proximal end engagement part 56 of the main manipulation part 6.

The transmission member 8 is inserted into the sixth insertion passage 711 to be advanceable, retractable, and rotatable with respect to the manipulation coupling part 71. In a state in which the auxiliary manipulation part 7 is not coupled to the main manipulation part 6, the distal end of the transmission member 8 is disposed at a substantially intermediate part of the sixth insertion passage 711 in the direction of the central axis L.

The stylet engagement part 82 is configured so that the stylet 5 and the transmission member 8 are engaged with each other when the proximal end engagement part 56 is inserted between the two arms 82b on the central axis L. When the stylet 5 and the transmission member 8 are engaged with each other, the planar parts 82c and 82d come into contact with the proximal end engagement part 56, and the rotational motion of the transmission member 8 can be transmitted to the stylet 5. Further, the stylet 5 can advance when the transmission member 8 advances.

The auxiliary manipulation part main body 72 has a tubular shape and is disposed on a distal end side of the auxiliary manipulation part 7. As represented in FIG. 14A, a seventh insertion passage 721 extending in the direction of the central axis L is formed in the auxiliary manipulation part main body 72. The seventh insertion passage 721 includes a first region 721a on a proximal end side thereof, and a second region 721b which is located on a distal end side from the first region 721a and has an opening diameter smaller than an opening diameter of the first region 721a. A first ring member 723 is externally fixed to an outer peripheral surface of a proximal end portion of the auxiliary manipulation part main body 72 and is fixed by a screw 724.

A connector 725 is fixed to a distal end portion of the auxiliary manipulation part main body 72. Specifically, the connector 725 is inserted to block a distal end opening of the second region 721b of the seventh insertion passage 721 and is fixed to the auxiliary manipulation part main body 72. An eighth insertion passage 726 is formed in the connector 725 along the central axis L, and a distal end portion of a guide tube 75 to be described later is fixed to a proximal end side of the eighth insertion passage 726. The cable tube 81 is fixed to a distal end side of the eighth insertion passage 726. The transmission member 8 is inserted into the guide tube 75 and the cable tube 81 fixed in the eighth insertion passage 726 and extends to the manipulation coupling part 71.

Figure 15:
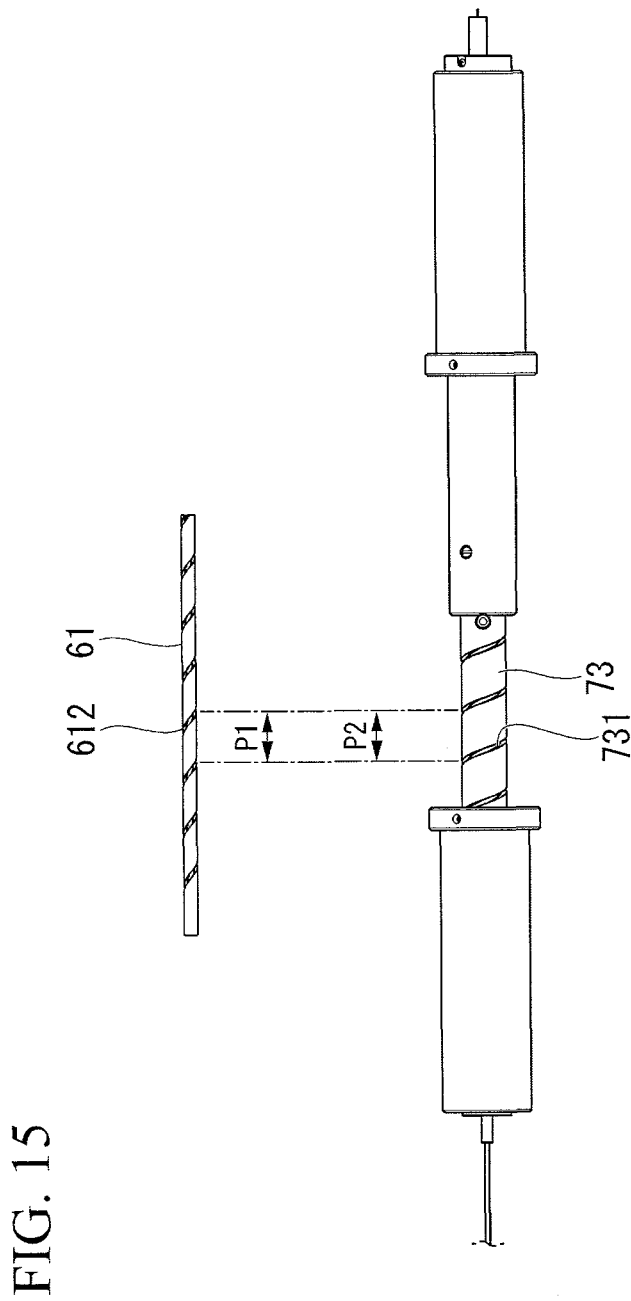
FIG. 15 is a diagram representing a relationship between the first guide passage and a second guide passage according to the embodiment of the present invention.

The second cam tube 73 is a long tubular member, and a second guide passage 731 configured of a groove that is formed in a spiral shape around the central axis L is formed on an outer circumferential surface of the second cam tube 73. As represented in FIG. 15, the second guide passage 731 of the second cam tube 73 and the first guide passage 612 of the first cam tube 61 are formed at the same spiral pitches P1 and P2 and in the same rotational direction. A distal end side of the second cam tube 73 is inserted through the first region 721a of the seventh insertion passage 721 of the auxiliary manipulation part main body 72, and a distal end portion of the second cam tube 73 is fixed to the second region 721b.

As represented in FIG. 14A, a gap S is formed between an inner peripheral surface of the first region 721a and an outer peripheral surface of the second cam tube 73. The second cam tube 73 has a cam insertion passage 732 extending in the direction of the central axis L. The cam insertion passage 732 is formed with a reduced diameter part 732a in which an opening diameter is reduced in a substantially central part in the direction of the central axis L.

The guide tube 75 having a length substantially equal to that of the second cam tube 73 is inserted into the cam insertion passage 732. A distal end portion of the guide tube 75 is fixed to the eighth insertion passage 726 of the connector 725 as described above. Since a proximal end side of the guide tube 75 is inserted through the reduced diameter part 732a of the cam insertion passage 732, the guide tube 75 is arranged so that a center thereof coincides with the central axis L. The transmission member 8 is inserted in the guide tube 75 to be advanceable and retractable. With this configuration, the transmission member 8 is supported on the central axis L to be advanceable and retractable within the auxiliary manipulation part 7.

As represented in FIGS. 13 and 14A, the rotation handle 74 is a tubular member, and is disposed at a proximal end portion of the auxiliary manipulation part 7. A ninth insertion passage 741 extending in the direction of the central axis L is formed in the rotation handle 74. An opening diameter of a distal end side region of the ninth insertion passage 741 is set to be slightly larger than an outer diameter of the second cam tube 73. Three screw holes 742 communicating an outer peripheral surface and the inside of the ninth insertion passage 741 are formed at a distal end portion of the rotation handle 74 (two screw holes 742 are not represented in FIG. 14A). Each of the screw holes 742 is provided at the same interval in the circumferential direction at every ⅓ turn (an angle of 120 degrees), and is provided at the same interval in the longitudinal direction at every ⅓ length of the aforementioned spiral pitch.

The second cam tube 73 is inserted into the ninth insertion passage 741. In the state in which the second cam tube 73 is inserted into the ninth insertion passage 741 of the rotation handle 74, a second engaging pin 743 is screwed and fixed to each of the screw holes 742. Each of the screw holes 742 protrudes into the ninth insertion passage 741, and a distal end portion thereof is engaged with the inside of the second guide passage 731. An outer diameter of a distal end portion of the second engaging pin 743 is smaller than an opening width of the second guide passage 731. Therefore, the distal end portion of the second engaging pin 743 is configured to be relatively movable inside the second guide passage 731 in accordance with the rotation of the rotation handle 74. The second cam tube 73 and the second engaging pin 743 constitute a second spiral mechanism 90.

A fixing member 744 that covers a proximal end opening of the ninth insertion passage 741 is fixed to a proximal end portion of the rotation handle 74. The proximal end portion of the transmission member 8 and the proximal end portion of the rotation handle 74 are fixed to each other by the fixing member 744. Therefore, the proximal end portion of the transmission member 8 follows the manipulation of the rotation handle 74. That is, the second spiral mechanism 90 advances the transmission member 8 while rotating the transmission member 8 with respect to the auxiliary manipulation part main body 72.

A second ring member 745 is externally fixed to an outer peripheral surface of a substantially central part of the rotation handle 74 in the direction of the central axis L and is fixed by a screw 746. An outer diameter of the rotation handle 74 on a distal end side of the second ring member 745 is set to be slightly smaller than the opening diameter of the first region 721a of the seventh insertion passage 721.

In the indwelling device 1 having the aforementioned configuration, the main manipulation part 6 can perform various manipulations such as advancement, retraction, and rotation of the sheath 3, advancement and retraction of the needle tube 4, and advancement, retraction, and rotation of the stylet 5. The auxiliary manipulation part 7 is configured such that advancement, retraction, and rotational manipulation of the transmission member 8 can be performed and manipulation on the needle tube 4 may not be performed.

Figure 16:
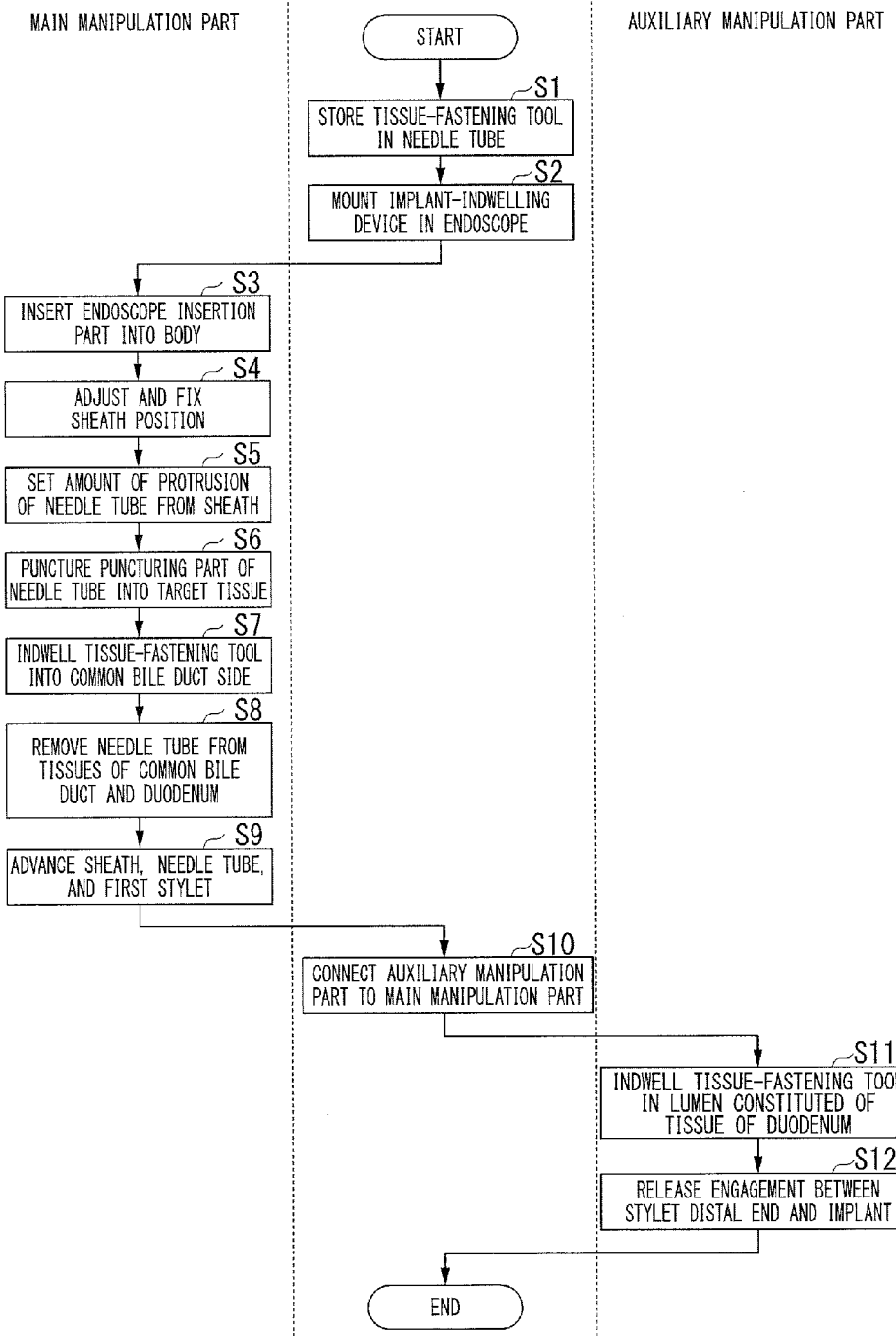
FIG. 16 is a flowchart of a procedure in which the endoscopic treatment tool according to the embodiment of the present invention is used.

Next, regarding the motion of the indwelling device 1, an example of a procedure of mounting the indwelling device 1 to an ultrasonic endoscope (hereinafter referred to as an "endoscope") and indwelling the tissue-fastening tool 2 to penetrate the tissue D of a duodenum and the tissue CBD of a common bile duct will be described. FIG. 16 is a flowchart representing the procedure of this embodiment.

The indwelling device 1 is configured such that a motion (a first motion) of moving the stylet 5 from the proximal end side to the distal end side with respect to the needle tube 4 can be manipulated by both of the main manipulation part 6 and the auxiliary manipulation part 7. Meanwhile, the indwelling device 1 is configured such that a manipulation (a second motion) of the needle tube 4 is performed only in the main manipulation part 6. This will be described in detail below.

Figure 17:
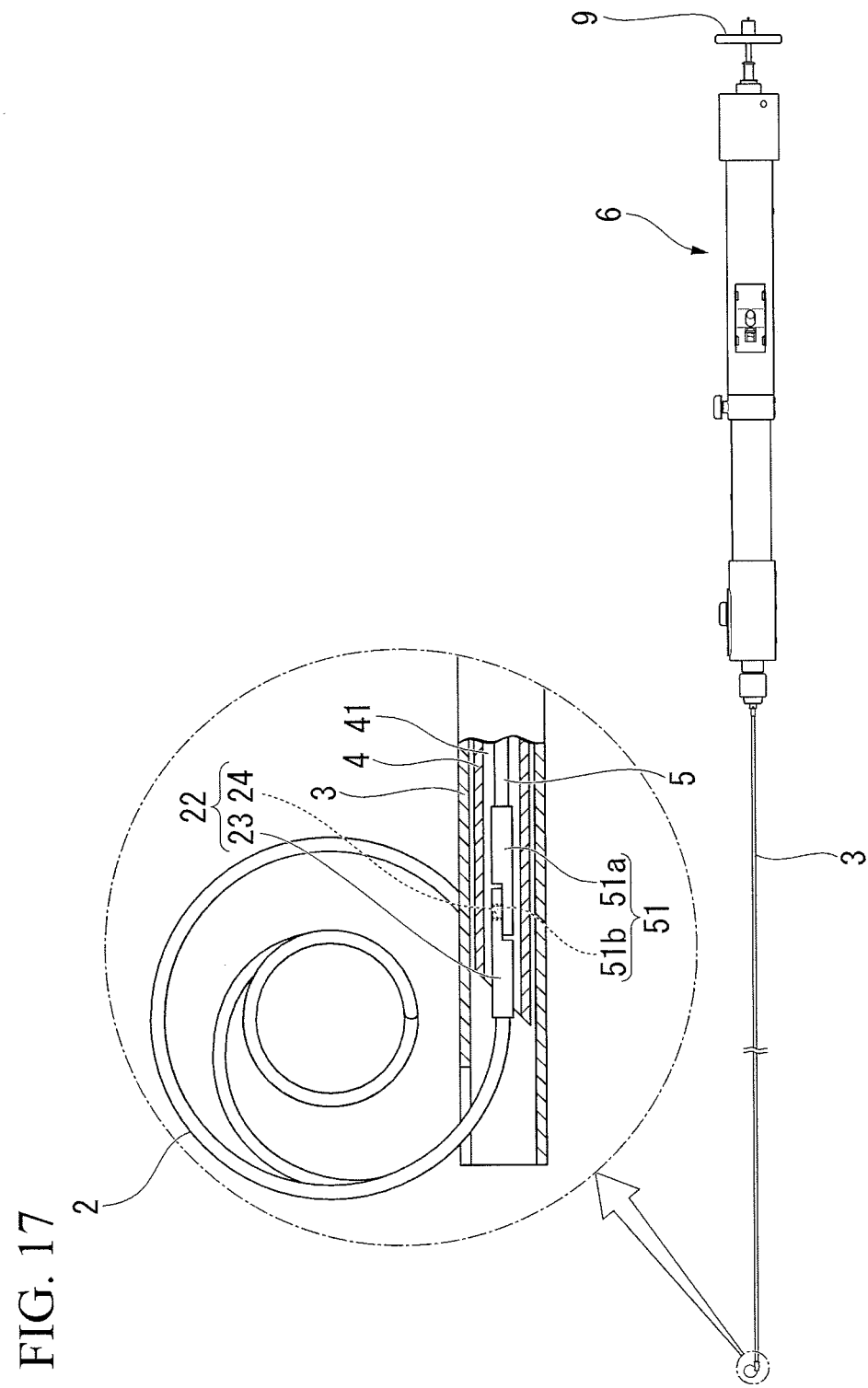
FIG. 17 is a side view representing an initial state of the main manipulation part according to the embodiment of the present invention.

FIG. 17 is a side view representing an initial state of the main manipulation part 6. As represented in FIG. 17, in the tissue-fastening tool 2, the distal end portion of the stylet 5 and the proximal end portion of the tissue-fastening tool 2 are engaged with each other inside the needle tube insertion passage 41 of the distal end portion of the needle tube 4 inserted into the sheath 3. The tissue-fastening tool 2 is provided to be projectable and retractable from the distal end of the needle tube 4. As represented in FIG. 17, a part of the tissue-fastening tool 2 located on a side closer to the distal end than the connection part with the stylet 5 protrudes from the distal end of the needle tube 4 and is disposed in a state in which a coil shape thereof is restored.

The main manipulation part 6 is packed as a product in a state in which the jig 9 is inserted from the proximal end side thereof.

If the state in which the entire tissue-fastening tool 2 is loaded in the needle tube 4 is set as a packing state, a state in which the tissue-fastening tool 2 is extended by the needle tube 4 continues for a long period of time. As a result, there is a possibility that a restoring force applied to the tissue-fastening tool 2 in advance to restore the coiled curved shape is weakened. When the tissue-fastening tool 2 is independently packed separately from the main manipulation part 6, it is necessary for a user to perform a task of coupling the proximal end portion of the tissue-fastening tool 2 and the distal end portion of the stylet 5. However, since the tissue-fastening tool 2 is a very small member, the coupling task requires skill and time.

In consideration of the reduction of the shape restoring force of the tissue-fastening tool 2 and difficulty of a loading task, in the present embodiment, as described above, the packing is performed in a state in which only the proximal end region of the tissue-fastening tool 2 engaged with the stylet 5 is inserted into the needle tube 4, and the distal end region thereof is exposed from the needle tube 4. This state is referred to as an initial state in this description. An example of a procedure for setting the initial state will be described below.

When the stylet 5 is moved to the extreme distal end side, the distal end engagement part 51 is exposed from the needle tube insertion passage 41. In this state, the initial state (packing state) is set by the protruding part 51b being engaged with the recessed part 24 of the tissue-fastening tool 2 and by the stylet 5 being moved to the proximal end side to store the distal end engagement part 51 in the needle tube 4. In the initial state, a connection state between the tissue-fastening tool 2 and the stylet 5 is maintained.

At this time, a motion of pulling the stylet 5 using the jig 9 is performed.

Figure 18:
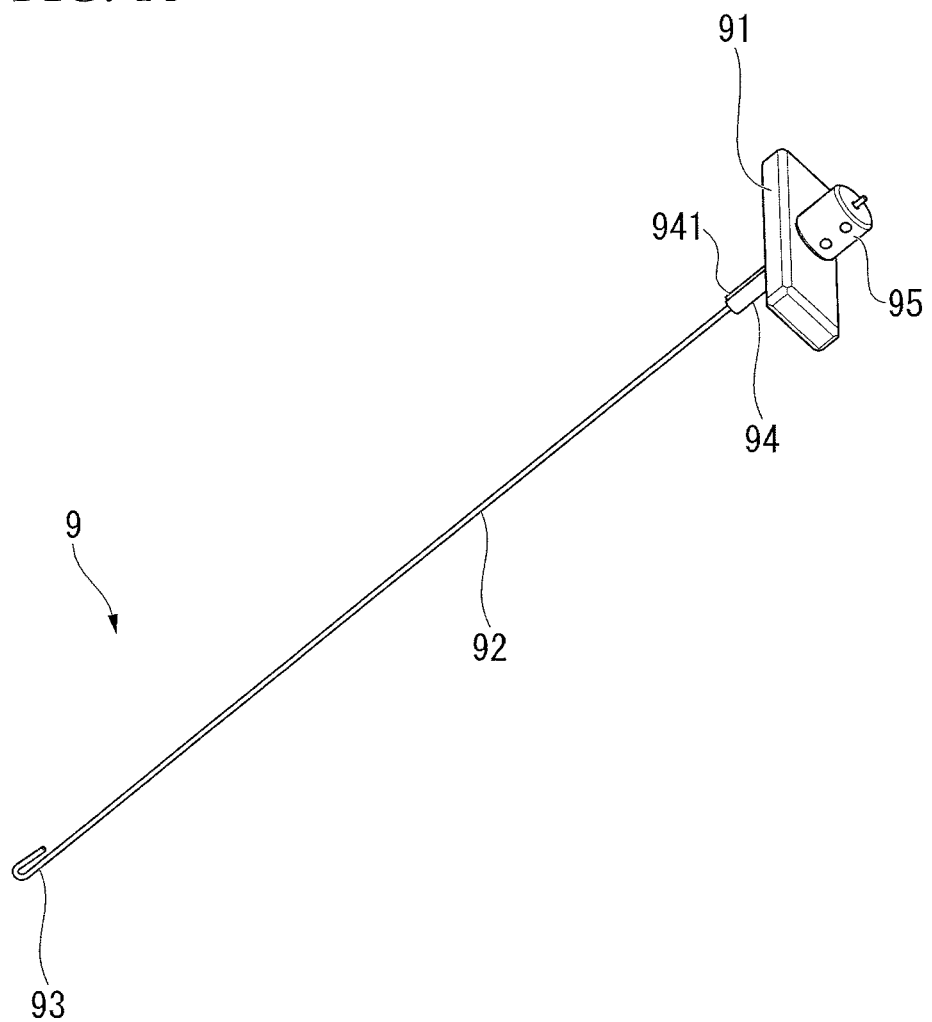
FIG. 18 is a perspective view of a jig according to the embodiment of the present invention.

The jig 9 is mounted on the main manipulation part 6 in the initial state (the packing state). FIG. 18 is a perspective view representing the jig 9. As represented in FIG. 18, the jig 9 includes a jig handle 91, a rod-like insertion shaft (a shaft) 92, a jig side coupling part 93, and a shaft head 95. The insertion shaft 92 is fixed to a distal end side of the shaft head 95. At the center of the jig handle 91, an open hole which is slightly larger than a diameter of the insertion shaft 92 and smaller than the shaft head 95 is formed, and the insertion shaft 92 is inserted through the hole. The jig side coupling part 93 has a hook shape which is curved from a distal end of the insertion shaft 92 and extends toward a proximal end side thereof. The jig handle 91 is provided to be relatively rotatable with respect to the insertion shaft 92. A tubular jig stopper 94 is externally mounted on an outer peripheral surface of a proximal end portion of the insertion shaft 92.

In the initial state, the jig side coupling part 93 is locked to the through-hole of the proximal end engagement part 56 in the first cam tube 61. That is, the tissue-fastening tool 2 and the jig 9 are connected to each other via the stylet 5.

The proximal end engagement part 56 is disposed on the distal end side of the first cam tube 61. The insertion shaft 92 passes through the inside of the first cam tube 61 and extends toward the proximal end side, and the jig handle 91 is exposed to the proximal end side of the main manipulation part 6. At this time, the jig stopper 94 is not externally mounted on the insertion shaft 92. The insertion shaft 92 has a length that is greater than or equal to a length from the proximal end engagement part 56 to the proximal end of the Luer joint 57 when the stylet 5 is located at the extreme distal end side with respect to the needle tube 4. At this time, since the distal end of the stylet 5 is exposed to the outside of the needle tube 4 as described above, the distal end of the stylet 5 is engaged with the tissue-fastening tool 2. The proximal end region of the tissue-fastening tool 2 is drawn into the needle tube 4 by pulling the jig 9 slightly toward the proximal end side to set the initial state. However, since there is a risk that the jig 9 moves toward the distal end side and the tissue-fastening tool 2 is detached in this state, the jig stopper 94 is mounted to prevent the jig 9 from moving to the distal end side in order to prevent the risk. Since a notch 941 is formed on the jig stopper 94 in the direction of the central axis L, the jig stopper 94 can be externally mounted on the insertion shaft 92 from a side thereof. Thus, the initial state (the packing state) is completed. After being sterilized by the manufacturer, a product is shipped.

First, a user performs a preparatory process (step S1) of pulling and entirely putting the tissue-fastening tool 2 into the needle tube 4. Here, the term "a user" refers to an operator and an assistant who assists a treatment of the operator. The preparatory process may be performed by the operator or by the assistant. In the following description, a rotational direction when the user performs a rotational manipulation of each part of the main manipulation part 6 and the auxiliary manipulation part 7 is represented as a rotational direction viewed from the proximal end to the distal end in the direction of the central axis L.

First, the user rotates the first rotation knob 66 of the main manipulation part 6 in a clockwise direction. When the first rotation knob 66 rotates in the clockwise direction, the Luer joint 57 and the first cam tube 61 fixed to the Luer joint 57 move to the proximal end side. Since the first engaging pin 55 of the stylet 5 is engaged with both the first guide passage 612 and the guide slit 673 of the needle guide 67, when the first cam tube 61 moves toward the proximal end side, the stylet 5 also moves toward the proximal end side. As a result, the tissue-fastening tool 2 is pulled toward the proximal end side within the needle tube 4. When the user continues to rotate the first rotation knob 66 clockwise, the female screw 661 comes in contact with a distal end side terminal of the male screw 572 of the Luer joint 57 screwed into the female screw 661, the first rotation knob 66 cannot rotate any more, and the movement of the Luer joint 57 to the proximal end side cannot be performed. Thus, the user perceives that the substantially intermediate part of the tissue-fastening tool 2 in the longitudinal direction has been drawn into the needle tube 4.

Next, the tissue-fastening tool 2 is drawn into the needle tube 4 using the jig 9. When the user pulls the jig handle 91 of the jig 9 toward the proximal side in the direction of the central axis L, a pulling force in a proximal end direction acts on the stylet 5. At this time, since the first engaging pin 55 slides along the first guide passage 612, the stylet 5 moves toward the proximal end side while rotating, and the tissue-fastening tool 2 is further drawn into the needle tube 4. The jig handle 91 is provided to be relatively rotatable with respect to the insertion shaft 92. Therefore, at a time of a manipulation in which the user pulls the jig handle 91 in the direction of the central axis L, the insertion shaft 92 rotates relative to the jig handle 91 to follow rotation of the stylet 5. At this time, since the first engaging pin 55 is also engaged with the guide slit 673 of the needle guide 67, the needle guide 67 is simultaneously rotated. Since the tissue-fastening tool 2 generates a strong force to return to an original coil shape thereof by being drawn into the needle tube 4, the needle tube 4 receives the strong force from the tissue-fastening tool 2. Therefore, the movement of the needle tube 4 in the rotational direction may be made to follow the movement of the tissue-fastening tool 2 in order to easily draw the tissue-fastening tool 2 into the needle tube 4. Therefore, the needle tube 4 is attached to the needle guide 67 to be relatively rotatable and not to be advanceable and retractable. The tissue-fastening tool 2 can be loaded into the needle tube 4 while rotating due to the motion of pulling the jig handle 91 toward the proximal end side in a linear direction along the central axis L.

When the user continues to draw the jig 9 toward the proximal side further, the tissue-fastening tool 2 is gradually stored in the needle tube 4, and one of the first engaging pins 55 that is disposed closest to the proximal end side comes in contact with an end surface on the distal end side of the Luer joint 57 immediately after the distal end of the tissue-fastening tool 2 is stored in the needle tube 4. Therefore, the stylet 5 can no longer move toward the proximal end side, and the jig 9 can no longer be drawn toward the proximal side. As a result, the user perceives that the loading of the tissue-fastening tool 2 has been completed. At the same time, since the proximal end engagement part 56 is exposed to the outside, the operator releases the engagement between the jig 9 and the proximal end engagement part 56 to detach the jig 9. Thus, the preparatory process is completed.

In this way, in the indwelling device 1 according to the present embodiment, since the tissue-fastening tool 2 is loaded using the jig 9, it is not required to provide a mechanism for drawing the tissue-fastening tool 2 into the needle tube 4 in the main manipulation part 6, and it is possible to reduce a size of the main manipulation part.

Figure 19:
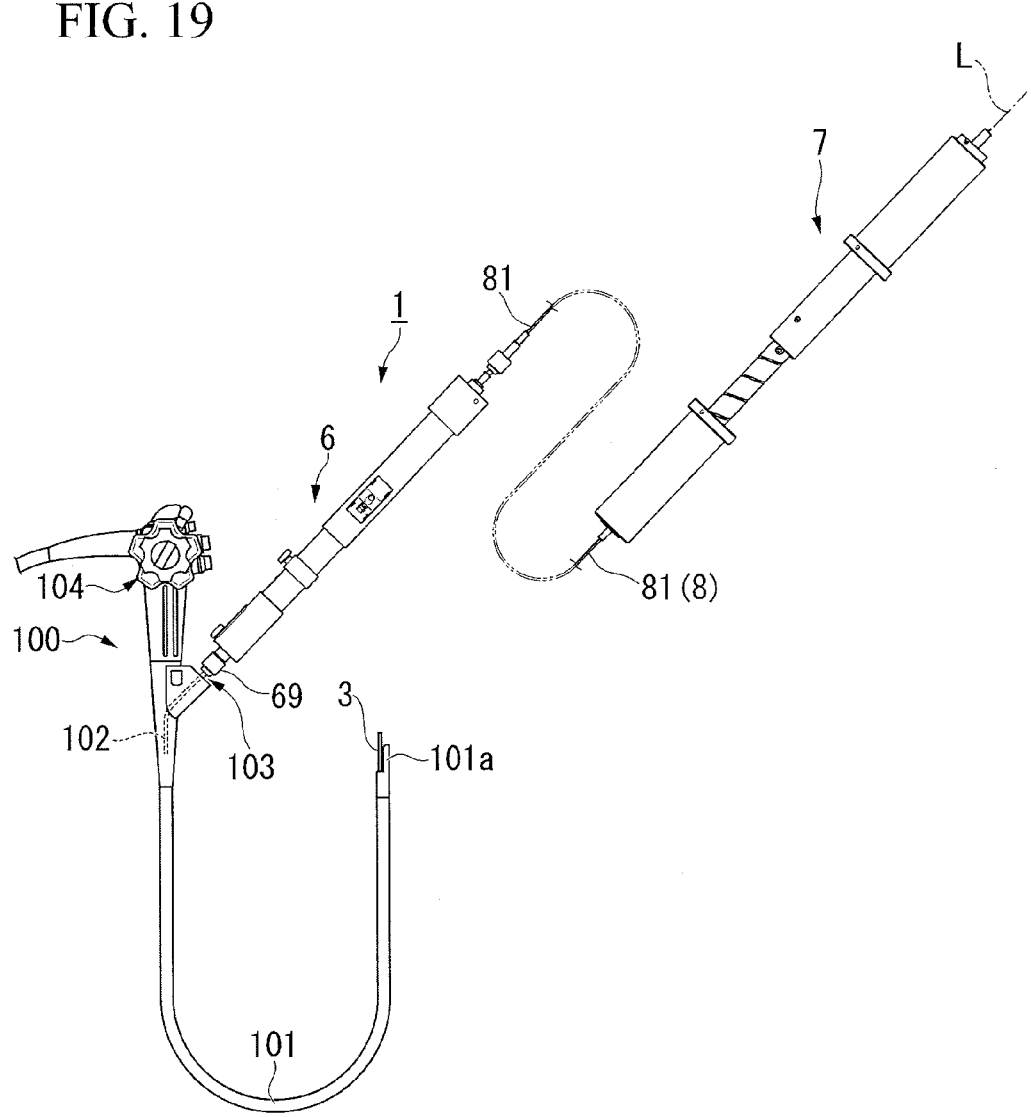
FIG. 19 is a diagram representing a state in which the endoscopic treatment tool according to the embodiment of the present invention is attached to an endoscope.

Next, the main manipulation part 6 is mounted on the endoscope 100 and fixed thereto (step S2). The sheath 3 and the needle tube 4 are inserted into the treatment tool channel 102 of the endoscope insertion part 101, and as represented in FIG. 19, the main manipulation part 6 is fixed to the manipulation part 104 of the endoscope 100 by the mounting part 69 provided at the distal end of the sheath slider 63 of the main manipulation part 6 being screw-engaged with the port 103 of the treatment tool channel 102 of the endoscope 100. In step S2, the operator and the assistant cooperate to perform the manipulation.

Figure 20:
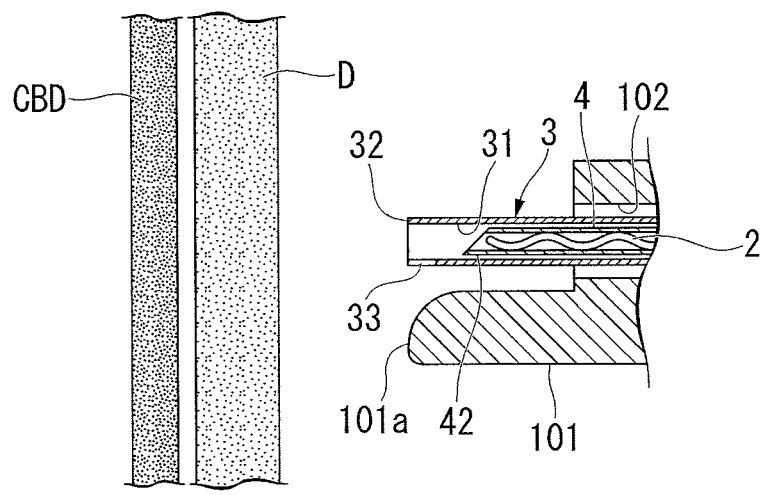
FIG. 20 is a side view representing a usage mode of the endoscopic treatment tool according to the embodiment of the present invention.

Manipulations from step S3 to step S9 are performed by the operator. FIGS. 20 to 26 are diagrams representing aspects on the distal end side of the endoscope insertion part 101 when using the indwelling device 1. As represented in FIG. 20, the operator inserts the endoscope insertion part 101 into a treatment target part in a body (step S3). A distal end of the endoscope insertion part 101 is inserted into the vicinity of the tissue D of the duodenum which is a target tissue.

Steps S2 and S3 may be performed in reverse order.

Next, a position of the distal end of the sheath 3 with respect to the distal end of the endoscope insertion part 101 is adjusted (step S4). The operator loosens the fixing knob 634 and advances and retracts the main manipulation part main body 62 in the direction of the central axis L with respect to the sheath slider 63 to adjust the position of the distal end of the sheath 3 in the direction of the central axis L so that the position becomes a feasible position with respect to the distal end of the endoscope insertion part 101. FIG. 20 represents a state in which the distal end position of the sheath 3 in the direction of the central axis L coincides with the distal end of the endoscope insertion part 101. When the distal end position of the sheath 3 is determined, the operator tightens the fixing knob 634 to fix the position of the sheath 3.

Figure 21:
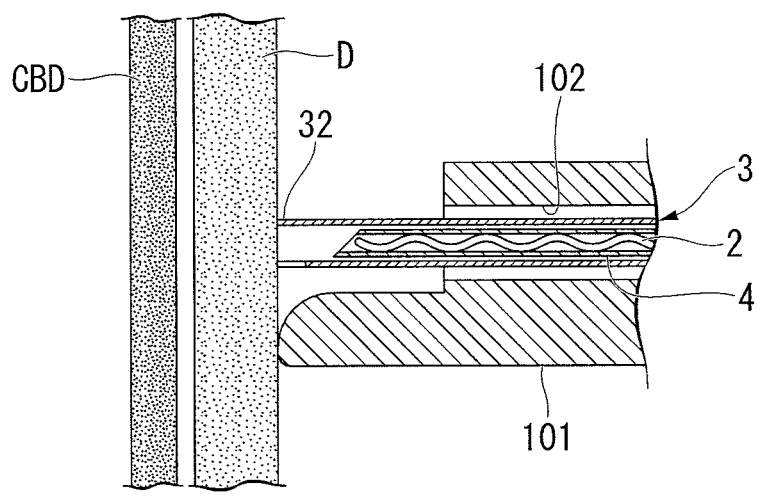
FIG. 21 is a side view representing the usage mode of the endoscopic treatment tool according to the embodiment of the present invention.

As represented in FIG. 21, the operator brings the endoscope insertion part 101 and the distal end opening portion 32 of the sheath 3 into contact with the tissue D of the duodenum. An ultrasonic transducer 101a is provided at the distal end of the endoscope insertion part 101. Therefore, in a subsequent treatment, a state in which the distal end of the endoscope insertion part 101 is in contact with the tissue D of the duodenum is maintained, and the operator performs the treatment while checking an ultrasonic image.

Subsequently, an amount of protrusion of the needle tube 4 from the distal end opening portion 32 of the sheath 3 in the direction of the central axis L is set (step S5). When the operator loosens the needle stopper screw 652, the needle slider stopper 65 can slide. After the operator slides the needle slider stopper 65 toward the distal end side depending on a length (amount of protrusion of the needle tube 4 from the sheath 3) by which the puncturing part 42 of the needle tube 4 is desired to puncture into the tissue, the operator tightens the needle stopper screw 652 to fix the needle slider stopper 65. By the manipulation, a puncture length of the puncturing part 42 of the needle tube 4 is set. At this time, the movement of the needle slider 64 is restricted by the slide button unit 68, and the needle slider 64 does not move linearly.

Figure 22:
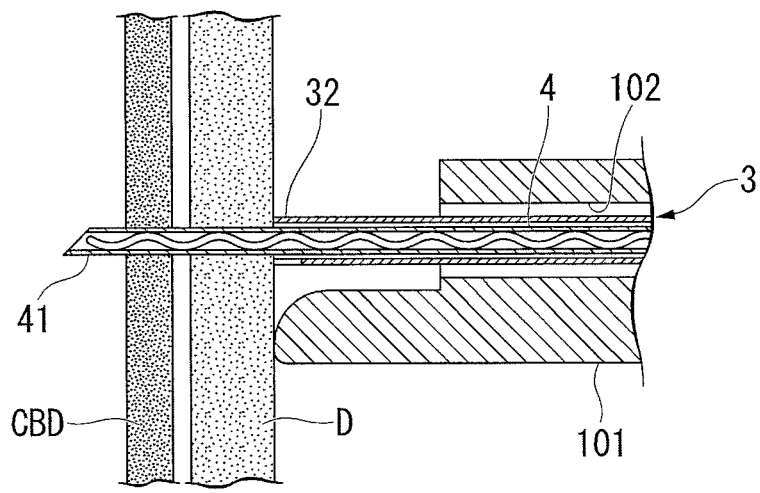
FIG. 22 is a side view representing the usage mode of the endoscopic treatment tool according to the embodiment of the present invention.

Next, as represented in FIG. 22, the puncturing part 42 of the needle tube 4 punctures the target tissue (step S6). When the operator pushes the button main body 682 of the slide button unit 68 toward the side of the central axis L, a restriction of an advancement and retraction movement of the needle slider 64 is released, and the needle slider 64 enters a state of being advanceable and retractable in the direction of the central axis L with respect to the main manipulation part main body 62. Thereafter, the operator advances the needle slider 64 in a linear direction until it comes into contact with the needle slider stopper 65. Since the needle slider 64 and the needle tube 4 are connected to each other via the needle guide 67 such that relative positions thereof in the direction of the central axis L are invariable, the needle tube 4 advances with the advancement of the needle slider 64. As a result, the puncturing part 42 of the needle tube 4 protrudes from the distal end of the sheath 3 and punctures the tissue D of the duodenum and the tissue CBD of the common bile duct, which are target tissues. When the operator releases his or her finger from the slide button unit 68, the slide button unit 68 moves in a direction which separates the button main body 682 from the outer side of the needle slider 64 in the radial direction by an urging force of the spring member 683, and the locking pin 684c is pressed against the outer surface of the main manipulation part main body 62.

Figure 23:
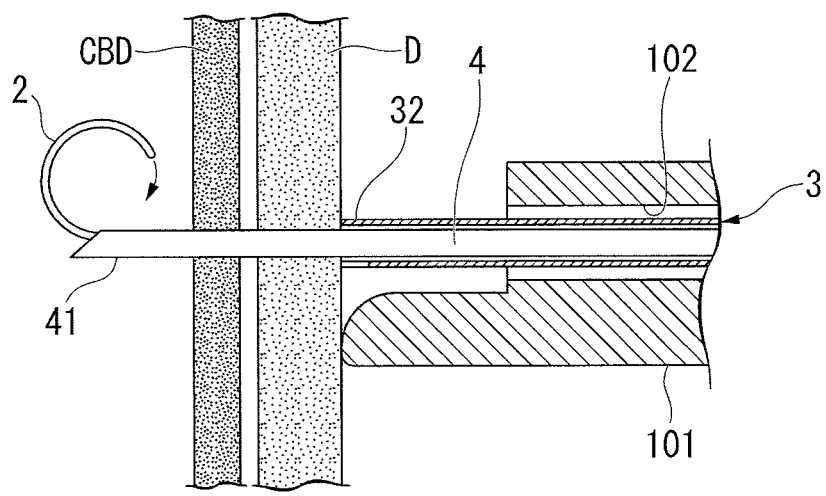
FIG. 23 is a side view representing the usage mode of the endoscopic treatment tool according to the embodiment of the present invention.

Next, the tissue-fastening tool 2 is indwelled into a common bile duct side (step S7). As represented in FIG. 23, the tissue-fastening tool 2 is protruded from the needle tube 4. The operator rotates the first rotation knob 66 counterclockwise.

When a counterclockwise rotational manipulation of the first rotation knob 66 is started, the needle slider 64 also rotates counterclockwise with the first rotation knob 66 until the locking pin 684c of the plate 684 is engaged with the spiral groove 622 of the main manipulation part main body 62. As soon as the locking pin 684c is engaged with the spiral groove 622, the needle slider 64 tries to advance toward the distal end side while rotating in accordance with the spiral groove 622. However, the needle slider 64 can neither rotate nor advance since the needle slider 64 is in contact with the needle slider stopper 65. Therefore, only the first rotation knob 66 rotates after the locking pin 684c is engaged with the spiral groove 622. When the first rotation knob 66 rotates with respect to the needle slider 64, the Luer joint 57 and the first cam tube 61 are linearly sent to the distal end side. At this time, since the end surface on the distal end side of the Luer joint 57 and one of the first engaging pins 55 at the extreme proximal end side come into contact with each other, the stylet 5 is linearly sent to the distal end side. As a result, a distal end side region of a coil of the tissue-fastening tool 2 is linearly sent from the distal end of the needle tube 4 into the common bile duct.

When a proximal end side end surface of the linear groove 573 of the Luer joint 57 comes into contact with a proximal end side end surface of the engaging projection 643b of the needle slider end member 643, the Luer joint 57 can no longer move toward the distal end side and the first rotation knob 66 does not rotate. A distance in the direction of the central axis L between the proximal end side end surface of the linear groove 573 of the Luer joint 57 and the proximal end side end surface of the engaging projection 643b of the needle slider end member 643 is set depending on a predetermined length at which the tissue-fastening tool 2 is sent on the common bile duct side. Therefore, as the first rotation knob 66 does not rotate, the operator can perceive that the process of indwelling the predetermined length of the coil of the tissue-fastening tool 2 on the common bile duct side is completed.

Figure 24:
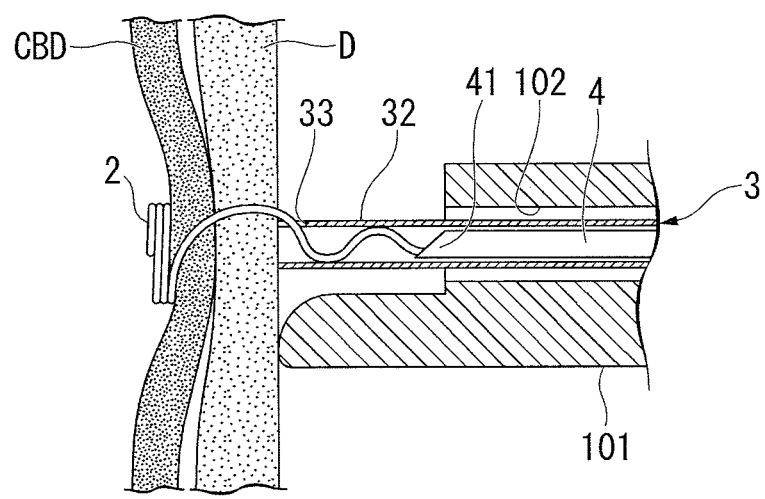
FIG. 24 is a side view representing the usage mode of the endoscopic treatment tool according to the embodiment of the present invention.

Next, as represented in FIG. 24, the needle tube 4 is removed from the tissue CBD of the common bile duct and the tissue D of the duodenum (step S8). When the needle tube 4 is removed, as the distal end of the needle tube 4 is pulled out of the tissue CBD of the common bile duct, a coil part 2a of the tissue-fastening tool 2 is inclined and a circumferential direction of the coil comes into close contact with the tissue CBD of the common bile duct. At this time, since there is a case in which the coil part 2a is inclined in a direction different from a predetermined direction of the coil, a manipulation of correcting a direction of the coil part 2a to the predetermined direction is necessarily performed.

The operator rotates the needle slider 64 clockwise. Since the locking pin 684c of the plate 684 is engaged with the spiral groove 622 of the main manipulation part main body 62, when the needle slider 64 is rotated clockwise, the needle slider 64 moves toward the proximal end side while rotating along the spiral groove 622. The Luer joint 57 and the first cam tube 61 also move toward the proximal end side while rotating clockwise together with the needle slider 64. Since the first guide passage 612 of the first cam tube 61 is formed in a right screw direction, by clockwise rotation of the first cam tube 61, an inner surface of the first guide passage 612 imparts a vector force in a direction of the proximal end side to the first engaging pin 55 of the stylet 5.

At this time, since the one of the first engaging pins 55 on the extreme proximal end side is in contact with the end surface on the distal end side of the Luer joint 57, the stylet 5 basically moves toward the proximal end side while rotating clockwise together with the needle slider 64. At this time, the needle guide 67 also moves toward the proximal end side while rotating clockwise together with the needle slider 64. Since the needle tube 4 is rotatably supported by the needle guide 67, the needle tube 4 moves toward the proximal end side together with the needle slider 64, but the movement of the needle tube 4 in the rotational direction is not related to the needle slider 64. In an actual procedure, since the endoscope insertion part 101 has a complex curved shape, the needle tube 4 inserted into the treatment tool channel 102 is also curved into a complicated shape. As described above, a material of the needle tube 4 is a metal tube, and it is difficult to perform a manipulation which rotates the needle tube 4 in a state of being curved into the complicated shape because a very strong force is necessary. Therefore, even if the needle slider 64 moves toward the proximal end side while rotating, the needle tube 4 is configured to only follow movement toward the proximal end side without rotating.

As represented in FIG. 6A, the sheath 3 is fixed to the sheath guide 623 via the sheath fixing part 625. The sheath guide 623 is rotatably supported by the main manipulation part main body 62.

As represented in FIG. 6D, the first slit 623b of the sheath guide 623 is fitted onto the rib 673a formed on the radial outside of the circumference of the guide slit 673 of the needle guide 67 to follow only the rotational direction. With such a configuration, when the needle slider 64 is moved toward the proximal end side while being rotated clockwise, the sheath 3 only follows the rotation.

With the aforementioned motion, the sheath 3 and the stylet 5 rotate while the needle tube 4 is pulled back. When the puncturing part 42 of the needle tube 4 is stored in the lumen 31 of the sheath 3, the wire of the tissue-fastening tool 2 enters the notched part 33 of the sheath 3. When the sheath 3 rotates in a predetermined direction in a state in which the wire of the tissue-fastening tool 2 is locked to the notched part 33, the coil part 2a indwelled in the common bile duct side rotates, and the direction of the coil part 2a is corrected to a desired state.

As described above, in step S8, the stylet 5 moves toward the proximal end side while rotating, and at the same time, the needle tube 4 moves toward the proximal end side without rotating. By this manipulation, since the stylet proximal end member 54 to which the stylet 5 is connected receives from the first cam tube 61 a vector in the direction toward the proximal end side, the stylet 5 and the needle tube 4 are pulled back toward the proximal end side. At this time, in a state in which the distal end opening portion 32 of the sheath 3 comes into contact with the target tissue, the coil part 2a of the tissue-fastening tool 2 indwelled in the common bile duct side acts as an anchor, and the tissue-fastening tool 2 simultaneously receives a force pulling in a direction of the distal end. When a force which pulls the stylet 5 toward the proximal end side increases, there is a risk that a force applied to the target tissue by the target tissue being sandwiched between the tissue-fastening tool 2 and the sheath 3 becomes stronger and the tissue is compressed due to an excessive load.

In the indwelling device 1 according to the present embodiment, in order to prevent an excessive load to the target tissue, when a force sandwiching the target tissue between the tissue-fastening tool 2 and the sheath 3 becomes stronger, synchronization of the stylet 5 with the movement of the needle slider 64 moving in the proximal end direction while rotating clockwise is released, and the force sandwiching the target tissue between the tissue-fastening tool 2 and the sheath 3 is relieved. As described above, the first guide passage 612 imparts the vector force in the direction of the proximal end side to the first engaging pin 55 of the stylet 5. However, when a force in the distal end direction from the tissue-fastening tool 2 becomes stronger than the vector force, the synchronization between the stylet 5 and the needle slider 64 is released, only the needle tube 4 moves toward the proximal end side, and the first engaging pin 55 moves in the distal end direction along the first guide passage 612. At this time, since the stylet 5 moves relative to the distal end side with respect to the needle slider 64, the load can be weakened. As a result, if the force in the distal end direction from the tissue-fastening tool 2 is lower than the vector force in the proximal end direction, the stylet 5 enters a state of following the movement of the needle slider 64 again. In this way, it is possible to prevent damage to the tissue of the treatment target site. A motion of automatically adjusting the load can be achieved by suitably setting the lead angle of the first guide passage 612. Specifically, the motion can be achieved by setting the lead angle within the range of 20 degrees to 75 degrees.

When the lead angle of the first guide passage 612 is smaller than 20 degrees, since the vector force in the proximal end side direction imparted to the first engaging pin 55 becomes stronger, forces are first balanced when the force in the distal end direction from the tissue-fastening tool 2 becomes very strong. Thus, there is a possibility that the sandwiched tissue is damaged. When the lead angle of the first guide passage 612 is larger than 75 degrees, since the vector force in the proximal end side direction imparted to the first engaging pin 55 becomes weaker, the forces are balanced in a state in which the force in the distal end direction from the tissue-fastening tool 2 is very weak. Thus, there is a possibility that the stylet 5 cannot be sufficiently pulled to the proximal end side. Further, it is more preferable that the lead angle be in the range of 40 degrees or more. This is because the larger the lead angle is, the smaller the diameter of the first cam tube 61 can be set. By reducing the diameter of the first cam tube 61, it is possible to reduce the diameter and weight of the main manipulation part 6.

In step S8, since the needle slider 64 does not rotate when the locking pin 684c moves toward the proximal end of the spiral groove 622, the operator can perceive that the needle tube 4 has been removed from the tissue.

Figure 25:
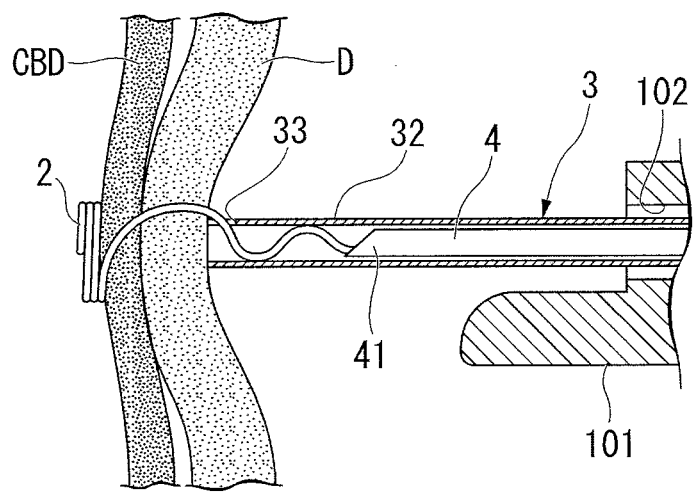
FIG. 25 is a side view representing the usage mode of the endoscopic treatment tool according to the embodiment of the present invention.

Next, as represented in FIG. 25, the sheath 3, the needle tube 4, and the stylet 5 are advanced by a predetermined distance (step S9). In a state in which the distal end portion of the sheath 3 comes into contact with the tissue D of the duodenum, the operator loosens the fixing knob 634 and advances the fixing knob 634 until the fixing knob 634 comes into contact with the distal end of the second slit 633. Thus, the main manipulation part main body 62 comes into contact with the distal end of the sheath slider 63. By this manipulation, the sheath 3 moves to the distal end side of the mounting part 69.

Since the mounting part 69 is fixed to the endoscope 100, the sheath 3 is extruded from the distal end of the endoscope insertion part 101, and the endoscope insertion part 101 relatively retracts and the distal end thereof is separated from the tissue D of the duodenum. In the subsequent treatment, a surgical field is imaged by an optical imaging device (not represented) provided at the distal end of the endoscope insertion part 101. The operator performs the treatment while checking the endoscopic image.

In step S9, a force in a direction of retracting toward the proximal end side is generated in the main manipulation part main body 62. However, since the screw part 634a of the fixing knob 634 is pressed by the resin spring 635 of the sheath slider 63, it is possible to prevent the main manipulation part main body 62 from retracting.

Since the main manipulation part main body 62 can no longer advance when the fixing knob 634 comes into contact with the distal end of the second slit 633, the operator can perceive that the main manipulation part main body 62 has been pushed into a predetermined position. Further, since the main manipulation part main body 62 does not unintentionally move toward the proximal end side due to the function of the resin spring 635 even if the fixing knob 634 is not tightened, the position of the main manipulation part main body 62 does not deviate from the predetermined position.

The next step S10 is performed by the assistant and the operator cooperating. Manipulations subsequent to step S11 are performed by the assistant manipulating the auxiliary manipulation part 7. That is, the manipulation of sending the coil of the tissue-fastening tool 2 to the duodenum side is performed by the auxiliary manipulation part 7.

The auxiliary manipulation part 7 is connected to the main manipulation part 6 (step S10). The assistant holds the auxiliary manipulation part 7 and inserts the proximal end of the Luer joint 57 of the main manipulation part 6 into the distal end opening of the sixth insertion passage 711 of the manipulation coupling part 71. When the operator or the assistant rotates the manipulation coupling part 71, the screw groove 712 of the sixth insertion passage 711 and the flange 574 formed at the proximal end portion of the Luer joint 57 are screwed together, and the main manipulation part 6 and the auxiliary manipulation part 7 are connected to each other. When the rotation handle 74 is rotated clockwise, the rotation handle 74 advances while rotating to follow the second guide passage 731 formed in the second cam tube 73. Since the transmission member 8 is fixed to the rotation handle 74 via the fixing member 744, the transmission member 8 advances while rotating clockwise. Since the stylet engagement part 82 of the transmission member 8 advances while rotating, the stylet engagement part 82 comes into contact with the proximal end engagement part 56 of the stylet 5 in a short time.

As represented in FIG. 8, the proximal end portion 56a has a shape that protrudes toward the proximal end side on the central axis L. Therefore, in a state in which the stylet engagement part 82 of the transmission member 8 and the proximal end of the proximal end engagement part 56 of the stylet 5 come into contact with each other, the transmission member 8 advances while rotating. Thus, the proximal end engagement part 56 of the main manipulation part 6 is fitted and engaged between the two arms 82b of the stylet engagement part 82. Thereafter, the rotation and the advance driving of the transmission member 8 can be transmitted to the stylet 5.

As represented in FIG. 19, since the main manipulation part 6 and the auxiliary manipulation part 7 are coupled to each other by a flexible part including the cable tube 81 and the transmission member 8, adaptability can be given to a positional relationship between the main manipulation part 6 and the auxiliary manipulation part 7. Thus, the assistant can perform the manipulation without disturbing the operator by standing at a location where it is easy to operate the auxiliary manipulation part 7. Since there is the flexible part between the main manipulation part 6 and the auxiliary manipulation part 7, the main manipulation part 6 is not strongly pushed even if the assistant strongly pushes the auxiliary manipulation part 7 in the distal end direction of the central axis L. Therefore, for example, it is possible to prevent an accident such as an extrusion of the needle tube 4 toward the distal end side due to a careless motion of the assistant without an intention of the operator.

Next, the tissue-fastening tool 2 is indwelled in a lumen constituted of the tissue D of the duodenum (step S11).

When the assistant rotates the rotation handle 74 clockwise, the transmission member 8 advances while rotating clockwise.

Specifically, as represented in FIG. 14A, when the rotation handle 74 is rotationally manipulated, the second engaging pin 743 moves along the inside of the second guide passage 731, and the rotation handle 74 moves relative to the distal end side with respect to the second cam tube 73 and approaches the auxiliary manipulation part main body 72. Further, when the rotation handle 74 is rotationally manipulated, the distal end portion of the rotation handle 74 enters the gap S between the second cam tube 73 and the auxiliary manipulation part main body 72 inside the first region 721a of the seventh insertion passage 721.

When the rotation handle 74 is rotationally manipulated as described above, the transmission member 8 is configured to advance while rotating with respect to the auxiliary manipulation part 7 and to protrude from the manipulation coupling part 71. As a result, the spiral movement (a spiral input) of the transmission member 8 is transmitted to the stylet 5.

The spiral pitch P1 of the first guide passage 612 of the first cam tube 61 is equal to the spiral pitch P2 of the second guide passage 731 of the second cam tube 73. Rotational directions of the first guide passage 612 and the second guide passage 731 are also equal to each other in the clockwise direction. The indwelling device 1 is provided with the main manipulation part 6 and the auxiliary manipulation part 7 as separate bodies, and the manipulation of the auxiliary manipulation part 7 is transmitted to the main manipulation part 6 via the transmission member 8. Further, in consideration of manipulation properties when the main manipulation part 6 and the auxiliary manipulation part 7 are manipulated by different persons, the transmission member 8 may have flexibility and may have a long length in some cases. In this case, there is a deviation between the movement of the rotation handle 74 and the movement of the stylet engagement part 82 due to an influence of bending and length of the transmission member 8 in the transmission path of the driving force, so that there is a possibility that movement may not be accurately transmitted to the stylet 5.

However, in the indwelling device 1 according to the present embodiment, since the first guide passage 612 and the second guide passage 731 are formed at the same spiral pitch and in the same rotational direction, a rotating motion transmitted from the transmission member 8 can be adjusted to be the same rotational movement amount as the movement of the rotation handle 74 in the first guide passage 612. Therefore, an input in a spiral direction generated by the rotational manipulation of the auxiliary manipulation part 7 is accurately output from the stylet 5 as a spiral motion.

Figure 26:
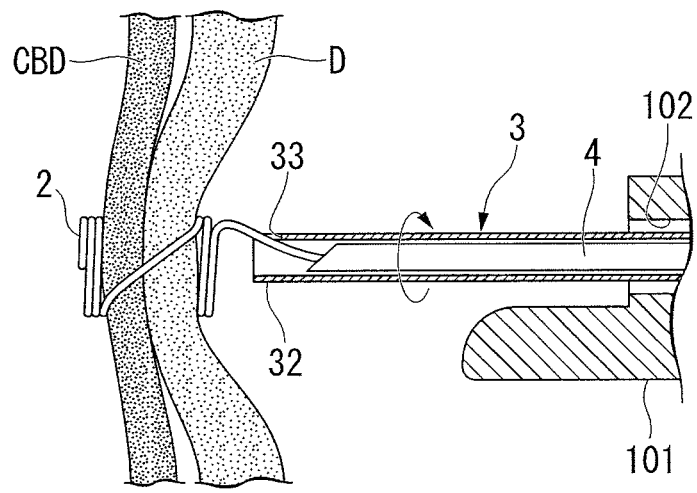
FIG. 26 is a side view representing the usage mode of the endoscopic treatment tool according to the embodiment of the present invention.

As described above, when the rotation handle 74 is rotationally manipulated, the first engaging pin 55 of the stylet 5 rotates the needle guide 67 and the needle guide 67 rotates the sheath guide 623. Thus, the sheath 3 rotates in synchronization with the rotation of the stylet 5. As illustrated in FIG. 26, in step S11, since the tissue-fastening tool 2 enters the notched part 33 of the sheath 3, the tissue-fastening tool 2 is pushed out from the needle tube 4 while being rotated by the sheath 3 and the stylet 5. At this time, the needle tube 4 does not rotate as described above. When the one of the first engaging pins 55 of the stylet 5 at the extreme distal end side comes into contact with the distal end of the first guide passage 612 of the first cam tube 61, the advancement of the stylet 5 is completed. At this time, the distal end of the stylet 5 is exposed to the outside of the needle tube 4.

Thus, the engagement between the implant-coupling part 22 of the tissue-fastening tool 2 and the distal end engagement part 51 of the stylet 5 is released (step S12), and the indwelling of the tissue-fastening tool 2 is completed. As described above, the indwelling device 1 is configured such that the distal end of the stylet 5 is exposed from the distal end of the needle tube 4 when both of the main manipulation part 6 and the auxiliary manipulation part 7 perform the motion (the first motion) in which the tissue-fastening tool 2 is discharged from the distal end of the needle tube 4 by the stylet 5 being advanced with respect to the needle tube 4.

According to the present embodiment, after the needle tube 4 is removed from the tissue and stored in the sheath 3, coil indwelling on the duodenum side is performed by the auxiliary manipulation part 7. That is, it is possible to separately perform a plurality of manipulations of the main manipulation part 6 and the auxiliary manipulation part 7 to indwell the tissue-fastening tool 2 in the treatment target tissue. Thus, the main manipulation part 6 can be reduced in size in comparison to a conventional implant-indwelling device. Therefore, it is possible to improve manipulation properties of the operator.

Furthermore, the manipulation related to the advancement and retraction of the needle tube 4 can be performed only by the main manipulation part 6, and a manipulation of the auxiliary manipulation part 7 is performed in a state in which the puncturing part 42 of the needle tube 4 is stored in the sheath 3. Therefore, only the operator can control the movement of the needle tube 4, and the puncturing part 42 cannot damage the tissue by the manipulation of the assistant. Therefore, a highly safe treatment can be performed.

According to the present embodiment, the main manipulation part is provided with the first spiral mechanism, and the auxiliary manipulation part is provided with the second spiral mechanism. Therefore, it is possible to output a manipulation that is input to the auxiliary manipulation part to the manipulation transmission member as a motion of the second spiral mechanism in a predetermined spiral direction. In addition, a motion which is input from the manipulation transmission member to the main manipulation part is once adjusted due to passing through the first spiral mechanism, and is output as a motion in the predetermined spiral direction from the stylet. Therefore, even if there is an error in an input motion input to the auxiliary manipulation part and an output motion output from the auxiliary manipulation part caused by a long drive transmission path between the main manipulation part and the auxiliary manipulation part, it is possible to adjust the error by the first spiral mechanism again. Therefore, a spiral motion which is input to the auxiliary manipulation part is transmitted to the tissue-fastening tool via the main manipulation part with high accuracy.

According to the present embodiment, since the lead angle of the first guide passage is set in the range of 20 degrees or more and 75 degrees or less, when a force sandwiching a target tissue between the tissue-fastening tool and the sheath becomes stronger, synchronization between the retraction of the needle tube and the retraction of the stylet is released. Therefore, it is possible to prevent an excessive load from being applied to the target tissue when removing the needle tube. More preferably, the lead angle is set in the range of 40 degrees or more. Since this enables a decrease in the diameter of the first cam tube, it is possible to reduce the diameter and weight of the main manipulation part.

According to the present embodiment, since the state in which the tissue-fastening tool is protruded from the distal end of the needle tube and packed is the initial state, the state in which the tissue-fastening tool is stretched within the needle tube for a long period of time is not maintained, and the fastening force of the tissue-fastening tool can be maintained in a suitable state.

Furthermore, the tissue-fastening tool in the packing state can be easily loaded using the jig. In the indwelling device according to the present embodiment, since the tissue-fastening tool is loaded using the jig, there is no need to provide the main manipulation part with a mechanism which draws the tissue-fastening tool into the needle tube, and the size of the main manipulation part can be reduced.

In the present embodiment, although the implant-indwelling device 1 is described using an example of the endoscopic treatment tool, the endoscopic treatment tool is not limited thereto. For example, a configuration such as a suction biopsy needle may be provided in which a specific motion in a treatment tool can be performed by a manipulation input from the auxiliary manipulation part in a state in which the main manipulation part and the auxiliary manipulation part are coupled to each other. When the endoscopic treatment tool is a suction biopsy needle, an example in which the biopsy needle is manipulated only by the main manipulation part and the stylet is manipulated by the main manipulation part and the auxiliary manipulation part exists.

Although the present embodiment describes the configuration in which the main manipulation part 6 and the auxiliary manipulation part 7 can be separated as an example, the main manipulation part and the auxiliary manipulation part may be configured to be inseparable, for example, by integrally configuring the stylet 5 and the transmission member 8.

The present embodiment describes an example in which the protruding part 51b is provided on the distal end engagement part 51, the recessed part 24 is provided in the implant-coupling part 22, and the stylet 5 and the tissue-fastening tool 2 are connected to each other by the protruding part 51b being engaged with the recessed part 24. However, a configuration in which the recessed part is provided in the distal end engagement part and the protruding part is provided in the implant engagement part may be adopted.

Although the present embodiment describes an example in which the three first engaging pins 55 are provided on the stylet proximal end member 54, the number of the first engaging pins is not limited to three, and at least one first engaging pin may be provided.

Although the present embodiment describes an example in which the first guide passage 612 is a hole communicating the inside and outside of the first cam tube 61 and the second guide passage 731 is a groove having a bottom formed on the outer peripheral surface of the second cam tube 73, for example, the second guide passage may be a hole.

While the embodiments of the present invention have been described in detail with reference to the drawings, the specific configuration is not limited to the embodiments and includes design changes and the like within a scope that does not depart from the gist of the present invention.

Further, the constituent elements described in each of the embodiments and each of the modified examples can be constituted by appropriately combining them.

The present invention is not limited by the foregoing description, and is only limited by the appended claims.

What is claimed is:

1. An endoscopic treatment tool set, comprising:
   an endoscopic treatment tool that includes:
      a sheath in which a lumen extending from a distal end to proximal end of the sheath is formed;
      an elongated shaft which passes through the lumen of the sheath, and the elongated shaft including an insertion passage therein;
      a stylet having a distal end part and a proximal end part, the stylet being disposed in the insertion passage to be movable relative to the elongated shaft, the distal end part of the stylet having a distal end engagement part;
      a stylet proximal end member having a distal end and a proximal end, the distal end of the stylet proximal end member being fixed to the proximal end part of the stylet, the proximal end of the stylet proximal end member having a proximal end engagement part;
      an implant including a proximal end portion connected to a distal end the distal end engagement part of the stylet in the insertion passage; and
      a main manipulation part provided at a proximal end side of the sheath; and
   a jig configured to be connected to the stylet, wherein the jig includes:
      a shaft which has a rod-like shape;
      a handle which is provided at a proximal end portion of the shaft of the jig; and
      a coupling part which has a hook shape which is curved at a distal end portion of the shaft of the jig,
   wherein the endoscopic treatment tool is packed in a package together with the jig in a packed state in which the proximal end portion of the implant is located inside the insertion passage and a distal end portion of the implant is exposed from the elongated shaft,
   wherein in the packed state in which the endoscopic treatment tool is packed in the package, the shaft of the jig is inserted into the main manipulation part from a proximal end of the main manipulation part, the handle of the jig protrudes from the proximal end of the main manipulation part, the coupling part of the jig is engaged with the proximal end engagement part of the stylet proximal end member disposed in the main manipulation part, and the implant is connected to the jig via the stylet, and
   wherein when the handle of the jig is pulled along a longitudinal axis of the main manipulation part, the stylet moves toward the proximal end of the main manipulation part in the insertion passage, and the whole of the implant is loaded inside the insertion passage.

2. The endoscopic treatment tool set according to claim 1, wherein
   a curved shape is imparted to the implant in advance, and
   a part of the implant exposed from the elongated shaft forms the curved shape in the packed state.

3. The endoscopic treatment tool set according to claim 1, wherein
   the coupling part of the jig is coupled to the stylet via the stylet proximal end member such that a rotation of the stylet around a longitudinal axis of the stylet and a movement of the shaft of the jig in a longitudinal axis of the shaft are linked with each other, and the handle of the jig supports the elongated shaft such that the elongated shaft rotates freely and the elongated shaft is movable toward a proximal end in the longitudinal axis of the elongated shaft.

4. The endoscopic treatment tool set according to claim 1, wherein the coupling part of the jig is releasably engaged with the proximal end engagement part of the stylet proximal end member.

5. The endoscopic treatment tool set according to claim 1, wherein
   the main manipulation part includes:
      a slider fixed to a proximal end of the elongated shaft and provided to be movable in an axis of the slider with respect to the main manipulation part;
      a Luer joint having a distal end surface, the Luer joint being configured to be retractable while rotating in accordance with a manipulation of the stylet; and
      a cam tube fixed to a distal end portion of the Luer joint, the cam tube having a guide groove formed on a surface of the cam tube with a helical shape around the longitudinal axis of the main manipulation part, the cam tube supporting the stylet proximal end member, and the cam tube being configured to rotate in accordance with a rotation of the Luer joint,
   wherein the coupling part of the jig is configured to be engaged with the proximal end engagement part of the stylet proximal end member at an inside of the cam tube.

6. The endoscopic treatment tool set according to claim 5, wherein a length of the shaft of the jig is equal to or longer than a length from the proximal end engagement part of the stylet proximal end member to a proximal end of the Luer joint when the stylet is located at the most distal side with respect to the elongated shaft.

7. The endoscopic treatment tool set according to claim 5, wherein the coupling part of the jig is releasably engaged with the proximal end engagement part of the stylet proximal end member.

8. The endoscopic treatment tool set according to claim 5, wherein the stylet proximal end member having a projection protruding radially outward from an outer circumference surface of the stylet proximal end member, the projection being positioned proximally to the distal end surface of the Luer joint, the projection is slidably engaged with the guide groove, and when the handle of the jig is pulled, the stylet moves to the proximal end of the main manipulation part and the projection slides along the guide groove, thereby moving the stylet toward the proximal end of the main manipulation part while being rotated around the longitudinal axis of the stylet and the implant is loaded inside the insertion passage.

9. The endoscopic treatment tool set according to claim 8, wherein when the projection comes in contact with the distal end surface of the Luer joint, the distal end portion of the implant is drawn into the elongated shaft.

10. The endoscopic treatment tool set according to claim 8, wherein the coupling part of the jig is releasably engaged with the proximal end engagement part of the stylet proximal end member.

* * * * *